(12) United States Patent
Melnick et al.

(10) Patent No.: US 8,703,503 B2
(45) Date of Patent: Apr. 22, 2014

(54) METHODS AND COMPOSITIONS FOR INHIBITION OF BCL6 REPRESSION

(75) Inventors: Ari M. Melnick, New York, NY (US); Jonathan D. Licht, Northbrook, IL (US); Gilbert Privé, Toronto (CA); Khaja Farid Ahmad, San Francisco, CA (US)

(73) Assignees: Albert Einstein School of Medicine of Yeshiva University, Bronx, NY (US); Mount Sinai School of Medicine, New York, NY (US)

( * ) Notice: Subject to any disclaimer, the term of this patent is extended or adjusted under 35 U.S.C. 154(b) by 0 days.

(21) Appl. No.: 12/932,304

(22) Filed: Feb. 23, 2011

(65) Prior Publication Data

US 2011/0286928 A1    Nov. 24, 2011

Related U.S. Application Data

(62) Division of application No. 10/582,662, filed as application No. PCT/US2004/042418 on Dec. 16, 2004, now Pat. No. 7,919,578.

(60) Provisional application No. 60/530,102, filed on Dec. 16, 2003.

(51) Int. Cl.
*G01N 33/566* (2006.01)
*C07K 14/00* (2006.01)
*A61K 38/00* (2006.01)

(52) U.S. Cl.
USPC ............................. 436/501; 530/350; 514/1.1

(58) Field of Classification Search
None
See application file for complete search history.

(56) References Cited

U.S. PATENT DOCUMENTS

| | | | |
|---|---|---|---|
| 7,612,181 B2 * | 11/2009 | Wu et al. | 530/387.3 |
| 7,919,578 B2 * | 4/2011 | Melnick et al. | 530/326 |
| 8,338,464 B2 * | 12/2012 | Melnick et al. | 514/365 |

* cited by examiner

*Primary Examiner* — Maury Audet
(74) *Attorney, Agent, or Firm* — Amster, Rothstein & Ebenstein LLP

(57) ABSTRACT

Provided are peptides or mimetics that block corepressor binding to a BCL6 lateral groove. Also provided are methods or blocking corepressor binding to the BCL6 lateral groove. Additionally, methods of inhibiting BCL6 repression in a mammalian cell, and methods of treating a mammal with cancer are provided.

14 Claims, 22 Drawing Sheets

E.

F.

METHODS AND COMPOSITIONS FOR INHIBITION OF BCL6 REPRESSION

CROSS-REFERENCE TO RELATED APPLICATIONS

This is a divisional of U.S. application Ser. No. 10/582,662, filed May 24, 2007, now U.S. Pat. No. 7,919,578 which is a U.S. national phase of PCT Application No. PCT/US2004/042418, filed Dec. 16, 2004, which claims priority to U.S. Provisional Application No. 60/530,102, filed Dec. 16, 2003.

This application incorporates by reference the Sequence Listing in the ASCII text file named 96700$_{13}$1697$_{13}$2.txt which was created Sep. 5, 2012 and which is 11 kilobytes in size.

STATEMENT REGARDING FEDERALLY SPONSORED RESEARCH OR DEVELOPMENT

The invention was made with government support under Grant Nos. CA 59936 AM and R21CA 99982, awarded by the National Institutes of Health. The government has certain rights in the invention.

BACKGROUND OF THE INVENTION (1) Field of the Invention

The present invention generally relates to inhibition of corepressor binding to BCL6. More specifically, the invention is directed to compositions and methods for inhibiting corepressor binding to the BCL6 lateral groove.

(2) Description of the Related Art

REFERENCES CITED

Adams, J., Kelso, R., and Cooley, L. (2000). The kelch repeat superfamily of proteins: propellers of cell function. Trends Cell Biol 10, 17-24.

Ahmad, K. F., Engel, C. K., and Privé, G. G. (1998). Crystal structure of the BTB domain from PLZF. Proc Natl Acad Sci USA 95, 12123-12128.

Albagli-Curiel, O. (2003). Ambivalent role of BCL6 in cell survival and transformation. Oncogene 22, 507-516.

Ball, H. J., Melnick, A., Shaknovich, R., Kohanski, R. A., and Licht, J. D. (1999). The promyelocytic leukemia zinc finger (PLZF) protein binds DNA in a high molecular weight complex associated with cdc2 kinase. Nucleic Acids Res 27, 4106-4113.

Ball, L. J., Jarchau, T., Oschkinat, H., and Walter, U. (2002). EVH1 domains: structure, function and interactions. FEBS Lett 513, 45-52.

Bardwell, V. J., and Treisman, R. (1994). The POZ domain: a conserved protein-protein interaction motif. Genes Dev 8, 1664-1677.

Baron, B. W., Anastasi, J., Thirman, M. J., Furukawa, Y., Fears, S., Kim, D. C., Simone, F., Birkenbach, M., Montag, A., Sadhu, A., et al. (2002). The human programmed cell death-2 (PDCD2) gene is a target of BCL6 repression: implications for a role of BCL6 in the down-regulation of apoptosis. Proc Natl Acad Sci U S A 99, 2860-2865.

Brunger, A. T., Adams, P. D., Cloare, G. M., DeLano, W. L., Gros, P., Grosse-Kunstleve, R. W., Jiang, J. S., Kuszewski, J., Nilges, M., and Pannu, N. S. (1998). Crystallography & NMR system: a new software suite for macromolecular structure determination. Acta Crystallographica D54, 905-921.

Calame, K. L., Lin, K. I., and Tunyaplin, C. (2003). Regulatory mechanisms that determine the development and function of plasma cells. Annu Rev Immunol 21, 205-230.

Costoya, J. A., and Pandolfi, P. P. (2001). The role of promyelocytic leukemia zinc finger and promyelocytic leukemia in leukemogenesis and development. Curr Opin Hematol 8, 212-217.

Cull, M. G., and Schatz, P. J. (2000). Biotinylation of proteins in vivo and in vitro using small peptide tags. Methods Enzymol 326, 430-440.

David, G., Alland, L., Hong, S. H., Wong, C. W., DePinho, R. A., and Dejean, A. (1998). Histone deacetylase associated with mSin3A mediates repression by the acute promyelocytic leukemia-associated PLZF protein. Oncogene 16, 2549-2556.

Deltour, S., Guerardel, C., and Leprince, D. (1999). Recruitment of SMRT/NCoR-mSin3A-HDAC-repressing complexes is not a general mechanism for BTB/POZ transcriptional repressors: the case of HIC-1 and gammaFBP-B. Proc Natl Acad Sci USA 96, 14831-14836.

Dent, A. L., Vasanwala, F. H., and Toney, L. M. (2002). Regulation of gene expression by the proto-oncogene BCL6. Crit Rev Oncol Hematol 41, 1-9.

Dhordain, P., Albagli, O. Ansieau, S., Koken, M. H., Deweindt, C., Quief, S., Lantoine, D., Leutz, A., Kerckaert, J. P., and Leprince, D. (1995). The BTB/POZ domain targets the LAZ3/BCL6 oncoprotein to nuclear dots and mediates homomerisation in vivo. Oncogene 11, Dhordain, P., Albagli, O., Lin, R. J., Ansieau, S., Quief, S., Leutz, A., Kerckaert, J. P., Evans, R. M., and Leprince, D. (1997). Corepressor SMRT binds the BTB/POZ repressing domain of the LAZ3/BCL6 oncoprotein. Proc Natl Acad Sci U S A 94, 10762-10767.

Dhordain, P., Lin, R. J., Quief, S., Lantoine, D., Kerckaert, J. P., Evans, R. M., and Albagli, O. (1998). The LAZ3(BCL6) oncoprotein recruits a SMRT/mSIN3A/histone deacetylase containing complex to mediate transcriptional repression. Nucleic Acids Res 26, 4645-4651.

Fearon, D. T., Manders, P., and Wagner, S. D. (2001). Arrested differentiation, the self-renewing memory lymphocyte, and vaccination. Science 293, 248-250.

Frankel, A. D. and Pabo, C. O. (1988). Cell 23, 1189-1193.

Grignani, F., De Matteis, S., Nervi, C., Tomassoni, L., Gelmetti, V., Cioce, M., Fanelli, M., Ruthardt, M., Ferrara, F. F., Zamir, I., et al. (1998). Fusion proteins of the retinoic acid receptor-alpha recruit histone deacetylase in promyelocytic leukaemia. Nature 391, 815-818.

Guidez, F., Ivins, S., Zhu, J., Soderstrom, M., Waxman, S., and Zelent, A. (1998). Reduced retinoic acid-sensitivities of nuclear receptor corepressor binding to PML- and PLZF-RARalpha underlie molecular pathogenesis and treatment of acute promyelocytic leukemia. Blood 91, 2634-2642.

Hamilton, A. C., Inglese, J., and Ferrer, M. (2003). A PDZ domain-based assay for measuring HIV protease activity: Assay design considerations. Protein Sci 12, 458-467.

He, L. Z., Guidez, F., Tribioli, C., Peruzzi, D., Ruthardt, M., Zelent, A., and Pandolfi, P. P. (1998). Distinct interactions of PML-RARalpha and PLZFRARalpha with co- repressors determine differential responses to RA in APL. Nat Genet 18, 126-135.

Hong, S. H., David, G., Wong, C. W., Dejean, A., and Privalsky, M. L. (1997). SMRT corepressor interacts with PLZF and with the PML-retinoic acid receptor alpha (RARalpha) and PLZF-RARalpha oncoproteins associated with acute promyelocytic leukemia. Proc Natl Acad Sci USA 94, 9028-9033.

Huynh, K. D., and Bardwell, V. J. (1998). The BCL6 POZ domain and other POZ domains interact with the co-repressors N-CoR and SMRT. Oncogene 17, 2473-2484.

Huynh, K. D., Fischle, W., Verdin, E., and Bardwell, V. J. (2000). BCoR, a novel corepressor involved in BCL6 repression. Genes Dev 14, 1810-1823.

Kaplan, J., and Calame, K. (1997). The ZiN/POZ domain of ZF5 is required for both transcriptional activation and repression. Nucleic Acids Res 25, 1108-1116.

Kay, B. K., Williamson, M. P., and Sudol, M. (2000). The importance of being proline: the interaction of proline-rich motifs in signaling proteins with their cognate domains. FASEB J 14, 231-241.

Kobayashi, A., Yamagiwa, H., Hoshino, H., Muto, A., Sato, K., Morita, M., Hayashi, N., Yamamoto, M., and Igarashi, K. (2000). A combinatorial code for gene expression generated by transcription factor Bach2 and MAZR (MAZ-related factor) through the BTB/POZ domain. Mol Cell Biol 20, 1733-1746.

Kreusch, A., Pfaffinger, P. J., Stevens, C. F., and Choe, S. (1998). Crystal structure of the tetramerization domain of the Shaker potassium channel. Nature 392, 945-948.

Kuppers, R., and Dalla-Favera, R. (2001). Mechanisms of chromosomal translocations in B cell lymphomas. Oncogene 20, 5580-5594.

Ladbury, J. E., Lemmon, M. A., Zhou, M., Green, J., Botfield, M. C., and Schlessinger, J. (1995). Measurement of the binding of tyrosyl phosphopeptides to SH2 domains: a reappraisal. Proc Natl Acad Sci USA 92, 3199-3203.

Lemercier, C., Brocard, M. P., Puvion-Dutilleul, F., Kao, H. Y., Albagli, O., and Khochbin, S. (2002). Class II histone deacetylases are directly recruited by BCL6 transcriptional repressor. J Biol Chem 277, 22045-22052.

Li, J. Y., English, M. A., Ball, H. J., Yeyati, P. L., Waxman, S., and Licht, J. D. (1997). Sequence-specific DNA binding and transcriptional regulation by the promyelocytic leukemia zinc finger protein. J Biol Chem 272, 22447-22455.

Li, X., Peng, H., Schultz, D. C., Lopez-Guisa, J. M., Rauscher, F. J., 3rd, and Marmorstein, R. (1999). Structure-function studies of the BTB/POZ transcriptional repression domain from the promyelocytic leukemia zinc finger oncoprotein. Cancer Res 59, 5275-5282.

Lin, R. J., Nagy, L., Inoue, S., Shao, W., Miller, W. H., Jr., and Evans, R. M. (1998). Role of the histone deacetylase complex in acute promyelocytic leukaemia. Nature 391, 811-814.

Lin, R. J., Sternsdorf, T., Tini, M., and Evans, R. M. (2001). Transcriptional regulation in acute promyelocytic leukemia. Oncogene 20, 7204-7215.

Mahmoudi, T., Katsani, K. R., and Verrijzer, C. P. (2002). GAGA can mediate enhancer function in trans by linking two separate DNA molecules. EMBO J 21, 1775-1781.

Melnick, A., Ahmad, K. F., Arai, S., Polinger, A., Ball, H., Borden, K. L., Carlile, G. W., Privé, G. G., and Licht, J. D. (2000). In-depth mutational analysis of the promyelocytic leukemia zinc finger BTB/POZ domain reveals motifs and residues required for biological and transcriptional functions. Mol Cell Biol 20, 6550-6567.

Melnick, A., Carlile, G., Ahmad, K. F., Kiang, C. L., Corcoran, C., Bardwell, V., Privé, G. G., and Licht, J. D. (2002). Critical residues within the BTB domain of PLZF and BCL6 modulate interaction with corepressors. Mol Cell Biol 22, 1804-1818.

Melnick, A., and Licht, J. D. (1999). Deconstructing a disease: RARalpha, its fusion partners, and their roles in the pathogenesis of acute promyelocytic leukemia. Blood 93, 3167-3215.

Ng D, Thakker N, Corcoran C M, Donnai D, Perveen R, Schneider A, Hadley D W, Tifft C, Zhang L, Wilkie A O, van der Smagt J J, Gorlin R I, Burgess S M, Bardwell V J, Black G C, Biesecker L G. (2004). Nat Genet. 36, 411-416.

Niu, H. (2002). The proto-oncogene BCL6 in normal and malignant B cell development. Hematol Oncol 20, 155-166.

Niu, H., Cattoretti, G., and Dalla-Favera, R. (2003). BCL6 Controls the Expression of the B7-1/CD80 Costimulatory Receptor in Germinal Center B Cells. J Exp Med 198, 211-221.

Otwinowski, Z., and Minor, W. (1997). Processing of X-ray diffraction data collected in oscillation mode. Methods in Enzymology: Macromolecular Crystallography Part A 276, 307-326.

Pasqualucci, L., Migliazza, A., Basso, K., Houldsworth, J., Chaganti, R. S., and Dalla-Favera, R. (2003). Mutations of the BCL6 proto-oncogene disrupt its negative autoregulation in diffuse large B-cell lymphoma. Blood 101, 2914-2923.

Pawson, T., and Nash, P. (2003). Assembly of cell regulatory systems through protein interaction domains. Science 300, 445-452.

Prehoda, K. E., Lee, D. J., and Lim, W. A. (1999). Structure of the enabled/VASP homology 1 domain-peptide complex: a key component in the spatial control of actin assembly. Cell 97, 471-480.

Scheldrick, G. M., and Schneider, T. R. (1997). SHELXL: high-resolution refinement. Methods Enzymol 277, 319-343.

Shaffer, A. L., Lin, K. I., Kuo, T. C., Yu, X., Hurt, E. M., Rosenwald, A., Giltnane, J. M., Yang, L., Zhao, H., Calame, K., and Staudt, L. M. (2002). Blimp-1 orchestrates plasma cell differentiation by extinguishing the mature B cell gene expression program. Immunity 17, 51-62.

Shaffer, A. L., Yu, X., He, Y., Boldrick, J., Chan, E. P., and Staudt, L. M. (2000). BCL6 represses genes that function in lymphocyte differentiation, inflammation, and cell cycle control. Immunity 13, 199-212.

Shen, H. M., Peters, A., Baron, B., Zhu, X., and Storb, U. (1998). Mutation of BCL6 gene in normal B cells by the process of somatic hypermutation of Ig genes. Science 280, 1750-1752.

Staudt, L. M. (2002). Gene expression profiling of lymphoid malignancies. Annu Rev Med 53, 303-318.

Stebbins, C. E., Kaelin, W. G., Jr., and Pavletich, N. P. (1999). Structure of the VHL-ElonginC-ElonginB complex: implications for VHL tumor suppressor function. Science 284, 455-461.

Sudol, M., Sliwa, K., and Russo, T. (2001). Functions of WW domains in the nucleus. FEBS Lett 490, 190-195.

Terwilliger, T. C., and Berendzen, J. (1999). Automated MAD and MIR structure solution. Acta Crystallogr D Biol Crystallogr 55 (Pt 4), 849-861.

Toney, L. M., Cattoretti, G., Graf, J. A., Merghoub, T., Pandolfi, P. P., Dalla-Favera, R., Ye, B. H., and Dent, A. L. (2000). BCL6 regulates chemokine gene transcription in macrophages. Nat Immunol 1, 214-220.

Wallace A C, Laskowski R A & Thornton J M (1995). LIGPLOT: A program to generate schematic diagrams of protein-ligand interactions. Prot. Eng., 8, 127-134.

Wang, X., Li, Z., Naganuma, A., and Ye, B. H. (2002). Negative autoregulation of BCL6 is bypassed by genetic alterations in diffuse large B cell lymphomas. Proc Natl Acad Sci USA 99, 15018-15023.

Wong, C. W., and Privalsky, M. L. (1998). Components of the SMRT corepressor complex exhibit distinctive interactions with the POZ domain oncoproteins PLZF, PLZF-RARalpha, and BCL6. J Biol Chem 273, 27695-27702.

Ye, B. H. (2000). BCL6 in the pathogenesis of non-Hodgkin's lymphoma. Cancer Invest 18, 356-365.

Zelent, A., Guidez, F., Melnick, A., Waxman, S., and Licht, J. D. (2001). Translocations of the RARalpha gene in acute promyelocytic leukemia. Oncogene 20, 7186-7203.

Zhang, H., Okada, S., Hatano, M., Okabe, S., and Tokuhisa, T. (2001). A new functional domain of Bcl6 family that recruits histone deacetylases. Biochim Biophys Acta 1540, 188-200.

The BTB domain is a highly conserved, widely distributed protein-protein interaction motif found in a family of transcription factors that play critical roles in cellular differentiation, development and neoplasia. Several BTB/zinc finger proteins, including B-cell lymphoma 6 (BCL6) and promyelocytic leukemia zinc finger (PLZF), are transcriptional repressors that are implicated in human malignancy (Albagli-Curiel, 2003; Costoya and Pandolfi, 2001; Dent et al., 2002; Lin et al., 2001; Melnick and Licht, 1999). Both the BCL6 and PLZF proteins consist of an N-terminal BTB domain, followed by a central region of several hundred residues that are predicted to have little or no fixed 3D structure, and end with a series of $C_2H_2$-type zinc finger domains at the C-terminus. This general type of architecture is seen in 43 of the over 200 known human BTB domain proteins (GGP and P. J. Stogios, http://xtal.uhnres.utoronto.ca/prive/btb.html). A second major class of BTB domain proteins contain C-terminal kelch β-propeller repeats, and many of these are thought to be involved in cytoskeletal functions, although some of these are involved in transcription regulation (Adams et al., 2000). The core BTB domain fold is also found in the T1 domain of voltage-gated $K^+$ channels (Kreusch et al., 1998), and in the ElonginC/Slcp1 proteins (Stebbins et al., 1999).

Despite the architectural similarity of the BTB/zinc finger transcription factors, these can function as repressors, activators, or both and the BTB domain plays a central role in these activities (Kaplan and Calame, 1997; Kobayashi et al., 2000; Mahmoudi et al., 2002). The majority of BTB/zinc finger proteins, however, are thought to be transcriptional repressors, and several of these mediate their effects through the recruitment of histone deacetylase complexes. Thus, in BCL6, the BTB domain mediates interactions with the SMRT, N-CoR, BCoR and mSin3A corepressors, as well as with histone deacetylase 1 (HDAC-1), and repression is relieved with HDAC inhibitors (David et al., 1998; Dhordain et al., 1997; Dhordain et al., 1998; Grignani et al., 1998; Guidez et al., 1998; He et al., 1998; Hong et al., 1997; Huynh and Bardwell, 1998; Huynh et al., 2000; Lin et al., 1998; Wong and Privalsky, 1998). The recruitment of a histone deacetylase complex is not a universal property of the BTB domain, as evidenced by the fact that the BTB domains of HIC1 and gFBP-B do not interact with these factors (Deltour et al., 1999). Thus, it is clear that distinct mechanisms are used by different BTB domains in order to carry out a variety of biological effects.

In the B-cell lineage, the BCL6 protein is expressed in germinal center (GC) B-cells, but not in pre-B cells or in differentiated progenies such as plasma cells. Because BCL6 expression is tightly regulated during lymphoid differentiation, its down-regulation in post-GC B-cells may be necessary for further plasma/memory cell differentiation. Some of the more notable genes that are repressed by BCL6 include the B lymphocyte-induced maturation protein (blimp-1), a transcriptional repressor of c-myc which plays a key role in differentiation of B-cells to plasma cells (Shaffer et al., 2002), the cell cycle control genes p27Icip1 and cyclin D2 (Shaffer et al., 2000), the programmed cell death-2 protein (PDCD2) (Baron et al., 2002), and B7-1/CD80 (Niu et al., 2003). Chromosomal translocations upstream of the BCL6 gene are observed in approximately 30-40% of diffuse large B-cell lymphomas (DLBCL) and in 5-14% of follicular lymphomas (FL) (Kuppers and Dalla-Favera, 2001; Niu, 2002; Ye, 2000). In addition, the promoter region of BCL6 is targeted by somatic hypermutation in GC B-cells (Pasqualucci et al., 2003; Shen et al., 1998; Wang et al., 2002). Thus, a B-cell with an activated BCL6 gene may be trapped at the GC stage due to the repression of differentiation and cell-cycle control proteins (Calame et al., 2003; Dent et al., 2002; Fearon et al., 2001; Staudt, 2002). In addition to its role in lymphoid cells, BCL6 represses the expression of the chemokines MCP-1, MCP3 and MRP-1 in macrophages and is an important negative regulator of TH-2 type inflammation (Toney et al., 2000).

Due to the importance of BCL6 in B-cell differentiation and leukemia development, there is a need for greater understanding of the mechanisms that control BCL6 interactions, particularly interactions with the corepressors SMRT, N-CoR and BCoR. The present invention addresses that need.

SUMMARY OF THE INVENTION

Accordingly, the invention is based on the identification of the BCL6 site of corepressor binding, and the discovery that peptides having the sequence of the corepressor binding site inhibit corepressor binding to BCL6. This inhibition causes apoptosis of B-cell lymphoma cells expressing BCL6.

Thus, in some embodiments, the invention is directed to compounds that are capable of blocking corepressor binding to a BCL6 lateral groove.

The invention is also directed to methods of blocking corepressor binding to the BCL6 lateral groove binding. The methods comprise contacting the BCL6 with any of the above-described compounds.

The invention is additionally directed to methods of inhibiting BCL6 repression in a mammalian cell. The methods comprise treating the cell with any of the above-described compounds.

In additional embodiments, the invention is directed to methods of treating a mammal with cancer, where the cancer requires BCL6 repression. The methods comprise administering any of the above-described compounds, in a pharmaceutically acceptable excipient, to the mammal.

The inventors have also identified a novel polypeptide that is a soluble form of the BCL6 BTB domain. This polypeptide comprises SEQ ID NO:12, which is BCL6 residues 5-129, with the point mutations C8Q, C67R and C84N. Thus, the invention is further directed to polypeptides comprising SEQ ID NO:12.

The invention is also directed to methods of determining whether a test compound inhibits corepressor binding to BCL6. The methods comprise determining whether the test compound binds to a BCL6 lateral groove, wherein a compound that binds to a BCL6 lateral groove inhibits corepressor binding to BCL6.

DETAILED DESCRIPTION OF THE INVENTION

Figure 1:
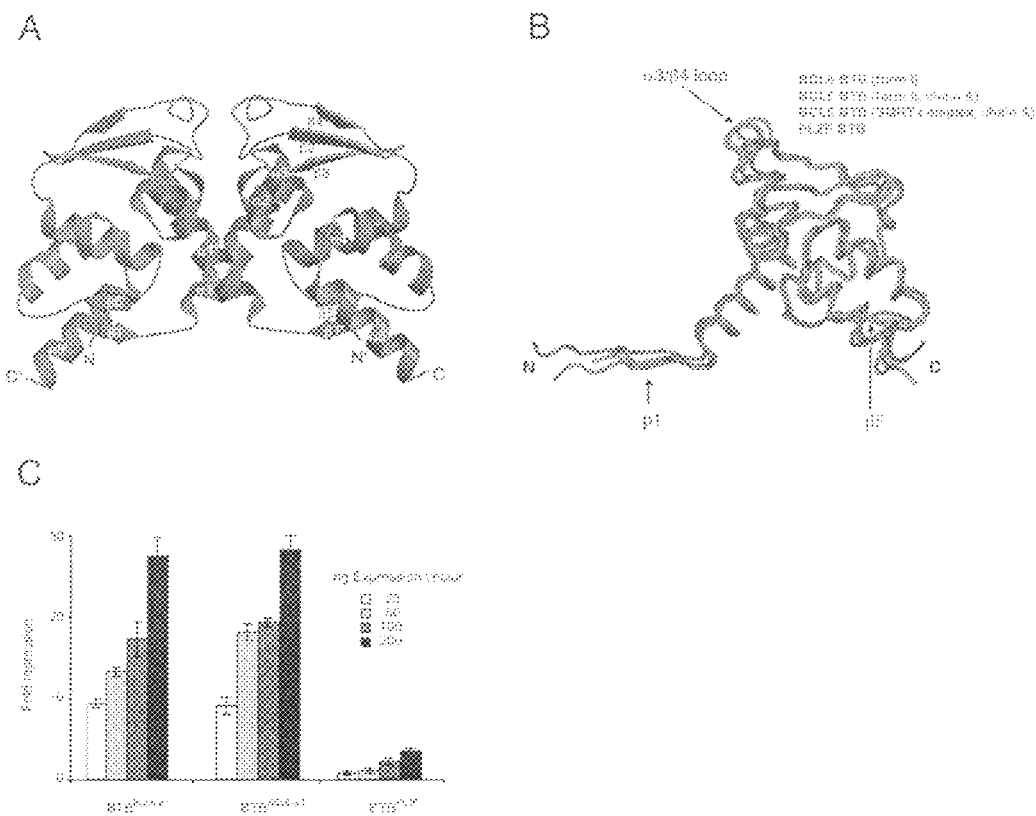
FIG. 1 is two diagrams and a graph showing the structure of the BCL6 BTB domain. Panel A is a ribbon diagram of the BCL6 BTB dimer (form I crystal). Panel B shows the superposition of single chains from various BTB domains structures. In all cases, the BTB domain forms highly similar homodimers. Panel C shows the results of reporter assays performed in 293 T cells comparing transcriptional repression mediated by escalating doses of vectors expressing the GAL4 DNA binding domain fused to the BTB domain from wild-type BCL6 (BTB$^{BCL.6\text{-}wt}$), C8Q/C67R/C84N cysteine substituted BCL6 (BTB$^{BCL6\text{-}3C}$), or PLZF (BTB$^{PLZF}$).

The present invention is based on the identification of the BCL6 site of corepressor binding, and the discovery that peptides having the sequence of the corepressor binding site inhibit corepressor binding to BCL6. This inhibition causes apoptosis of B-cell lymphoma cells expressing BCL6. See Examples.

Thus, in some embodiments, the invention is directed to compounds that bind to the BCL6 lateral groove and prevent corepressor binding. Based on the work described in the Examples, the skilled artisan could design many such compounds. These embodiments are not narrowly limited to any particular compound, and the compound can be, for example, an organic molecule less than 3000, 2000, 1500 or 1000 molecular weight, or an aptamer, both of which can be designed or identified by known methods. In preferred embodiments, the compound is a peptide or mimetic. These peptides or mimetics preferably comprise the sequence xxxxzxxxxxsx(w/h)xzpx, where x is any amino acid or mimetic analog and z is a non-polar amino acid or mimetic analog. That sequence represents a composite sequence of SEQ ID NO:s 1-3, which are shown in the examples to bind to the BCL6 lateral groove, preventing corepressor binding.

As used herein, "mimetics", also known as peptidomimetics, includes any of the many known compounds that behave like peptides, but are made of L-amino acid analogs that are more resistant to degradation than peptides. Examples include peptide analogs, pseudopeptides, depsipeptides, or, preferably, retro-inverso peptides or mimetics of D-amino acids. Any of these peptidomimetics to any particular peptide can be synthesized by the skilled artisan without undue experimentation.

Numerous examples of the invention peptides or mimetics can be identified by comparing the sequences of the BCL6 lateral groove binding sites from the SMRT, N-CoR, and BCoR corepressors, provided herein as SEQ ID NO:s 1-9 (see Appendix for identification of each sequence). The 17mers identified as SEQ ID NO:s 1-3 is the minimum sequence to achieve maximal inhibition of corepressor binding, but larger sequences, including 84mers, or longer, are also effective.

With the information provided in the Examples, the skilled artisan could identify numerous peptide sequences that would bind to the BCL6 lateral groove and inhibit corepressor binding, simply by aligning the residues of the three corepressor sequences (SEQ ID NO:1-3) and identifying sequences that combine the aligned residues, or providing conservative substitutions to the amino acids or analogs. Thus, any sequence within SEQ ID NO:10, which represents all possible combinations of the residues of SEQ ID NO:1-3, would be expected to inhibit binding of corepressors SMRT, N-CoR, and BCoR. Preferably, the peptide or mimetic comprises the sequence of SEQ ID NO:1, SEQ ID NO:2, or SEQ ID NO:3.

The peptides or mimetics can comprise any of amino acids or analogs as the lateral groove binding moiety, up to 84 or more, including 28 or less, 21 or less, or the minimal 17 amino acid or analog residues. The peptide or mimetic can even include the entire corepressor (i.e., SMRT, BCoR or N-CoR) sequence, where the sequence is mutated to prevent the peptide or mimetic from functioning as a corepressor.

The peptide or mimetic can also comprise one or more functional groups, such as a moiety that facilitates purification, e.g., a (His)$_6$ moiety or an antibody-binding epitope. Another functional group that can be utilized as part of the peptide or mimetic is a moiety that facilitates entry of the peptide or mimetic into a cell, such as the protein transduction domain from the HIV pTAT protein. An additional useful functional group here is a moiety that facilitates detection of the peptide or mimetic, such as a fluorescent moiety, a radioactive moiety, or an antigen. As a preferred example of a useful peptide comprising functional moieties, see the peptide WP, described in Example 2, which consists of the 2 mer having the sequence of SEQ ID NO:4, along with a (His)$_6$ moiety, the protein transduction domain from the HIV pTAT protein, and a hemagglutinin epitope tag for immunodetection of the peptide.

For therapeutic uses, the peptide or mimetic is preferably in a pharmaceutically acceptable excipient. Such compositions can be formulated without undue experimentation for administration to a mammal, including humans, as appropriate for the particular application.

Additionally, proper dosages of the compositions can be determined without undue experimentation using standard dose-response protocols.

Accordingly, the peptide or mimetic compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The peptide or mimetic compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical peptide or mimetic compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the peptide or mimetic composition may also take place using a nasal tampon or nasal sponge.

In additional embodiments, the invention is directed to methods of blocking corepressor binding to a BCL6 lateral groove. The methods comprise contacting the BCL6 with any of the compounds described above.

In preferred embodiments of these methods, the BCL6 is in a mammalian cell, preferably a cancer cell that requires BCL6 repression. Addition of the peptides to such cells cause apoptosis in a significant percentage of the cells (Example 2).

It is preferred that cancer cells treated in these methods are in a living mammal. The invention methods would be expected to work in any mammal, however, in the most preferred embodiments, the mammal is a human. Additionally, it is preferred that the cancer cell in these embodiments is a lymphoma cell or breast cancer cell, since those forms of cancer often require BCL6 repression to avoid apoptosis.

It is preferred in these methods that the compound comprises a peptide or mimetic that comprises the sequence of SEQ ID NO:10, most preferably SEQ ID NO:1, SEQ ID NO:2 or SEQ ID NO:3.

In other embodiments, the invention is directed to methods of inhibiting BCL6 repression in a mammalian cell. The methods comprise treating the cell with any of the above-described compounds. As with the methods described above, the cell is preferably a cancer cell, most preferably a lymphoma or a breast cancer cell. It is also preferred that the cell is in a mammal, most preferably a human. It is also preferred that the compound comprises a peptide or mimetic having the sequence of SEQ ID NO:1, SEQ ID NO:2 or SEQ ID NO:3.

In related embodiments, the invention is directed to methods of treating a mammal with cancer. The methods comprise administering any of the above described compounds, in a pharmaceutically acceptable excipient, to the mammal. In these methods, the cancer requires BCL6 repression. As such, treatment with the peptide prevents corepressor binding and causes apoptosis of the cell.

In preferred embodiments, the mammal is a human; it is also preferred that the cancer is a lymphoma or a breast cancer. As with the methods described above, the preferred compound comprises a peptide or mimetic comprising the sequence of SEQ ID NO:10, most preferably SEQ ID NO:1, SEQ ID NO:2. or SEQ ID NO:3.

The invention is additionally directed to methods of determining whether a test compound inhibits corepressor binding to BCL6. The methods comprise determining whether the test compound binds to a BCL6 lateral groove, where a compound that binds to a BCL6 lateral groove inhibits corepressor binding to BCL6. In these methods, the compound can be identified by any known method that utilizes the BCL6 lateral groove structural information provided in Examples 1 and 2.

These methods can employ a library screening protocol, i.e., where a library of compounds is screened for lateral groove binding. Preferably, however, the methods utilize the structure of the BCL6 lateral groove to aid in the design of a molecule that would be expected to bind to the BCL6 lateral groove and inhibit corepressor binding.

The skilled artisan could design the particular format for these methods by utilizing known procedures, For examples, the methods could employ an in vitro or an in vivo procedure (i.e., in cell culture), as utilized in Examples 1 or 2.

These methods are not limited to the compound that could be tested. The compound can, e.g., be an organic compound less than 1000, or 2000, or 3000 molecular weight. Alternatively, the compound can be an aptamer. In preferred embodiments, the compound is a peptide or mimetic.

The inventors have also identified a novel polypeptide that is a soluble form of the BCL6 BTB domain. This polypeptide comprises SEQ ID NO:12, which is BCL6 residues 5-129, with the point mutations C8Q, C67R and C84N. Thus, the invention is further directed to polypeptides comprising SEQ ID NO:12. As established in Example 1, this polypeptide is very useful for testing compounds for the ability to inhibit corepressor binding to BCL6. Also as established in Example 1, this polypeptide can be a fusion protein with other useful components, as described above. Also useful are polynucleotides encoding this polypeptide, and vectors comprising this polynucleotide.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Mechanism of SMRT Corepressor Recruitment by the BCL6 BTB Domain

Example Summary

BCL6 encodes a transcription factor that represses genes necessary for the terminal differentiation of lymphocytes within germinal centers, and the misregulated expression of this factor is strongly implicated in several types of B-cell lymphoma. The homodimeric BTB domain of BCL6 (also known as the POZ domain) is required for the repression activity of the protein, and interacts directly with the SMRT and N-CoR corepressors that are found within large multi-protein histone deacetylase-containing complexes. We have identified a 17 residue fragment from SMRT that binds to the BCL6 BTB domain, and determined the crystal structure of the complex to 2.2 Å. Two SMRT fragments bind symmetrically to the BCL6 BTB homodimer and, in combination with biochemical and in vivo data, the structure provides insight into the basis of transcriptional repression by this critical B-cell lymphoma protein.

Introduction

Given the important role of BCL6 in cellular differentiation and oncogenesis, we performed an in depth structural analysis to determine the mechanism through which BCL6 recruits the corepressors needed to mediate its silencing effects.

Results

BCL6 BTB domain structure. We crystallized the BTB domain from BCL6 under two different conditions (form I and form II) and solved its structure in the two distinct packing environments to 1.3 Å and 2.2 Å, respectively (Table 1 and FIG. 1). It was necessary to mutate three non-conserved cysteines to prevent aggregation of the recombinant protein (C8Q/C67R/C84N). This mutated BCL6 BTB domain had essentially the same activity as the wild-type protein in transcriptional repression assays (FIG. 1C). In all of the following sections of this example, the in vitro experiments involving purified BCL6 BTB domain were done on the form with the three substituted cysteines, while all cellular assays were done in the wild-type background.

Residues 1414-1430 of SMRT interact with the BCL6 BTB domain. The highly related corepressors N-CoR and SMRT (also known as N-CoR II) have an overall pairwise sequence identity of 45%, and large segments of these proteins are predicted to be intrinsically disordered. We have previously demonstrated the direct binding of murine N-CoR (residues 1351-1616) and human SMRT (residues 1414-1498) to the BCL6 BTB domain (Melnick et al., 2002). A shorter SMRT fragment from positions 1414 to 1441 binds to the BCL6 BTB domain with similar affinity (data not shown), and we used this as a basis for determining the minimal interaction fragment in SMRT. A series of N and C terminal deletions were made to SMRT$^{1414-1441}$ and the binding of these fragments to the BCL6 BTB domain was assessed in a

TABLE 1

Crystallographic statistics

|  | Form I (seMet) |  | Form I (native) | Form II | Complex |
| --- | --- | --- | --- | --- | --- |
| Resolution (Å) | 2.10 | 2.10 | 2.10 | 1.30 | 2.20 | 2.20 |
| Wavelength (Å) | 0.97947 | 0.97925 | 0.95742 | 0.8980 | 1.54 | 1.54 |
| Unique Reflections | 6586 | 6600 | 6719 | 27157 | 10909 | 16405 |
| Redundancy | 7.1 | 7.2 | 7.2 | 3.7 | 3.4 | 3.6 |
| Completeness % | 96.2 (73.8) | 96.4 (74.8) | 98.2 (87.8) | 95.7 (93.7) | 95.0 (85.3) | 99.2 (92.1) |
| <I>/<σI> | 21.7 (6.2) | 21.7 (7.5) | 24.7 (9.1) | 24.4 (4.3) | 12.8 (3.2) | 24.0 (3.7) |
| Rsym (%) | 9.3 (23.3) | 8.7 (20.6) | 6.8 (17.7) | 5.1 (30.2) | 9.2 (28.1) | 5.0 (25.6) |

| Refinement | Form I (native) | Form II | Complex |
| --- | --- | --- | --- |
| Resolution (Å) | 30.0-1.30 | 30.0-2.20 | 30.0-2.20 |
| Space group | C2 | C2 | P2$_1$ |
| Unit cell |  |  |  |
| a (Å) | 30.61 | 140.75 | 54.23 |
| b (Å) | 71.85 | 32.66 | 38.54 |
| c (Å) | 55.41 | 48.63 | 76.66 |
| β (°) | 105.9 | 94.73 | 92.92 |
| Data cutoff F/σ(F) | 0 | 0 | 0 |
| R/R$_{free}$, 5% (%) | 12.83/17.30 | 20.0/24.97 | 22.66/26.77 |
| RMSD bond lengths (Å) | 0.0130 | 0.0095 | 0.0097 |
| RNSD bond angles (°) | 1.53 | 1.40 | 1.40 |
| Number of atoms/residues |  |  |  |
| BTB$^{BCL6}$ | 1000/122 | 1972/244 | 2002/248 |
| SMRT-BBD | 0 | 0 | 274/36 |
| Waters | 188 | 1130 | 132 |

Numbers in parentheses refer to the high resolution shell (2.18-2.10 Å for Form I SeMet, 1.35-1.30 Å for Form I native, 2.28-2.20 Å for Form II and 2.28-2.20 Å for Complex).

As expected, the BCL6 BTB domain is structurally homologous to the PLZF BTB domain (Ahmad et al., 1998; Li et al., 1999), and forms a tightly interwound butterfly-shaped homodimer with an extensive hydrophobic interface. A least squares superposition of the crystallographically unique chains of the BCL6 BTB structures reported in this study with the BTB domain of PLZF (Ahmad et al., 1998) reveals virtually identical structures, with an average pairwise RMSD value of 1.0 Å for equivalent Cα atoms (FIG. 1B). The N-terminus of each chain is associated with the main body of the partner chain, generating a two-stranded antiparallel β-sheet between β1 of one monomer and strand β5' of the other. The domain is an obligate homodimer, with no evidence of exchange between subunits (KFA and GGP, unpublished observations).

The principle dimer contacts between the BCL6 BTB subunits are mediated by β1, α2, β5 and α6. Prominent surface features of the dimer include a conserved groove formed by the two α3/β4 loops at the "top" of the dimer, and an extensive hydrophobic concave surface formed by β1/α6'/β1'/α6 on the distal "bottom" side of the dimer.

co-purification assay in which the corepressor peptides were expressed as fusion proteins with histidine-tagged thioredoxin (Trx) (FIG. 2A,B).

Surface plasmon resonance (SPR) biosensor measurements were used to measure the relative strengths of interactions between the corepressor fragments and the BCL6 BTB domain (FIG. 2C,D). We measured a dissociation constant of 15.8±3 nM for the interaction of SMRT$^{1414-1414}$ and the BCL6 BTB domain (FIG. 2C), and interestingly, a. 2.5-fold stronger affinity of the BTB domain for the equivalent N-CoR$^{1351-1383}$ peptide (FIG. 2D). The relative binding affinities of the truncated and mutant SMRT peptides were largely in agreement with the copurification results, however, the SPR analysis revealed slightly weaker binding by SMRT$^{1417-1441}$ relative to SMRT$^{1414-1414}$, suggesting that residues 1414-1416 make a small but significant contribution to the overall strength of the interaction. We observed stronger binding of SMRT$^{1414-1430}$ relative to the two longer SMRT peptides, and this may be due to the presence of a free C-terminal carboxyl group in this fragment. From this analysis, the minimal fragment in SMRT required for interaction with the BCL6 BTB domain ranges from residues Leu-1414 to Arg-1430, and we used this fragment for further studies. We refer to this segment of the SMRT/N-CoR corepressors as the BCL6 binding domain (BBD).

We compared the measured dissociation constant from SPR with the value obtained in solution by isothermal titration calorimetry (ITC) (FIG. 2E). In solution, SMRT$^{1414-1430}$ (SMRT-BBD) binds to the BCL6 BTB domain with a $K_d$ of 11.4±1 µM, a value considerably less than from the SPR measurements. The stoicheometry of the interaction by ITC is 1.11 ±0.06 SMRT peptides per BCL6 chain, and since the BTB domain is an obligate homodimer, these results indicate that two peptides bind per protein dimer. There is no indication of cooperativity. The ITC measurements reveal a favorable enthalpic contribution ($\Delta H$=−23.2±1.6 kcal/mol) and an unfavorable entropic contribution (−T$\Delta S$=16.4±2.3) to the free energy of the interaction.

A micromolar dissociation constant is similar to the affinity observed for SH3 (Kay et al., 2000), WW (Sudol et al., 2001) and EVH1 (Ball et al., 2002) domains and their respective peptide binding partners. The stronger association as measured by SPR may be due to the fact that solid-phase techniques often overestimate binding affinities, and differences with solution phase measurements are often attributed to favorable avidity effects when one component is immobilized (Ladbury et al., 1995). Thus, for example, the affinities of the NHERF PDZ1 domain with carboxy-terminal peptides are typically in the nanomolar range when measured with SPR or cellular systems, but are found to be in the micromolar range when measured in homogenous solutions by techniques such as fluorescence polarization or ITC (Hamilton et al., 2003). We expect that avidity effects are important in this system because of the bivalent nature of the BCL6 BTB domain/BBD interaction.

We failed to measure any interaction between the PLZF BTB domain and any of the SMRT or N-CoR fragments by either the co-purification assay, SPR or ITC. We previously showed that the interaction of the PLZF BTB domain with the SMRT and N-CoR fragments was at the limit of detectability by the co-purification assay (Melnick et al., 2002), and with improvements to the method, we now conclude that any associations between these peptides and the PLZF BTB domain are not measurable by these techniques.

Structure of the BCL6 BTB Domain/SMRT-BBD Complex. The human BCL6 BTB domain was co-crystallized with the SMRT-BBD peptide in a form with an entire BTB dimer and two SMRT peptides in the asymmetric unit. Two SMRT-BBD chains associate with the BCL6 BTB dimer in the complex, resulting in an overall 2:2 binding ratio (Table 1, FIGS. 3 and 4). Each corepressor fragment binds in an extended conformation along a shallow groove formed at the BTB dimer interface, making extensive contacts with both chains of the BTB dimer and burying approximately 1080 Å$^2$ of surface area per peptide.

Although circular dichroism (CD) spectroscopy indicates that the unliganded SMRT fragment is unstructured in solution, the peptide in the complex is well defined and adopts a fixed conformation. The two crystallographically unique SMRT chains are virtually identical, and superpose with a Cα RMSD of 0.65 Å (FIG. 4E) and have very similar side chain conformations. There are no SMRT/SMRT contacts, and we describe the interactions of only one of the two corepressor chains with the BTB domain (the yellow chain in FIGS. 3 and 4), as essentially all the interactions are conserved across each of the two SMRT/BTB dimer interfaces.

There are only minor adjustments to the BCL6 BTB domain side chains upon complex formation, most notably in residues Arg-13, Arg-24, and His-116. In the unliganded structures, these amino acids have significantly higher side chain temperature factors relative to their neighboring residues. These adopt multiple conformations across the form I and form II crystals, and some of these conformers partially block the ligand binding groove. However, in the SMRT complex, these three residues are well-structured and make some of the more important ligand contacts (FIG. 3E). For example, in order to accommodate the SMRT fragment, Arg-13 swings out of the ligand binding groove, forms a hydrogen bond with Asp-17 from the same BCL6 chain, and makes numerous polar and non-polar contacts with the peptide.

The main chain torsion angles of the corepressor peptide all lie within the β-strand region of the Ramachandran plot, with the exception of Gly-1422 and Ser-1424, which are in the α-helical region. This causes a kink in the middle of the peptide, allowing the C-terminal half of the fragment to run up the front of the BTB dimer. Residues from both BTB chains contact each of the SMRT peptides, with contributions mainly from β1' and α1' from one BCL6 BTB chain, and α2, α3 and α6 from the other. The peptide binding interface is mostly polar, and the majority of protein-peptide interactions are mediated through backbone and sidechain hydrogen bonds, as well as through water-mediated hydrogen bonds. Both sites contain six bridging waters that contact both the peptide and the BTB domain (FIG. 4E), and three of these waters are also found in the unliganded BCL6 BTB crystals.

Figure 2:
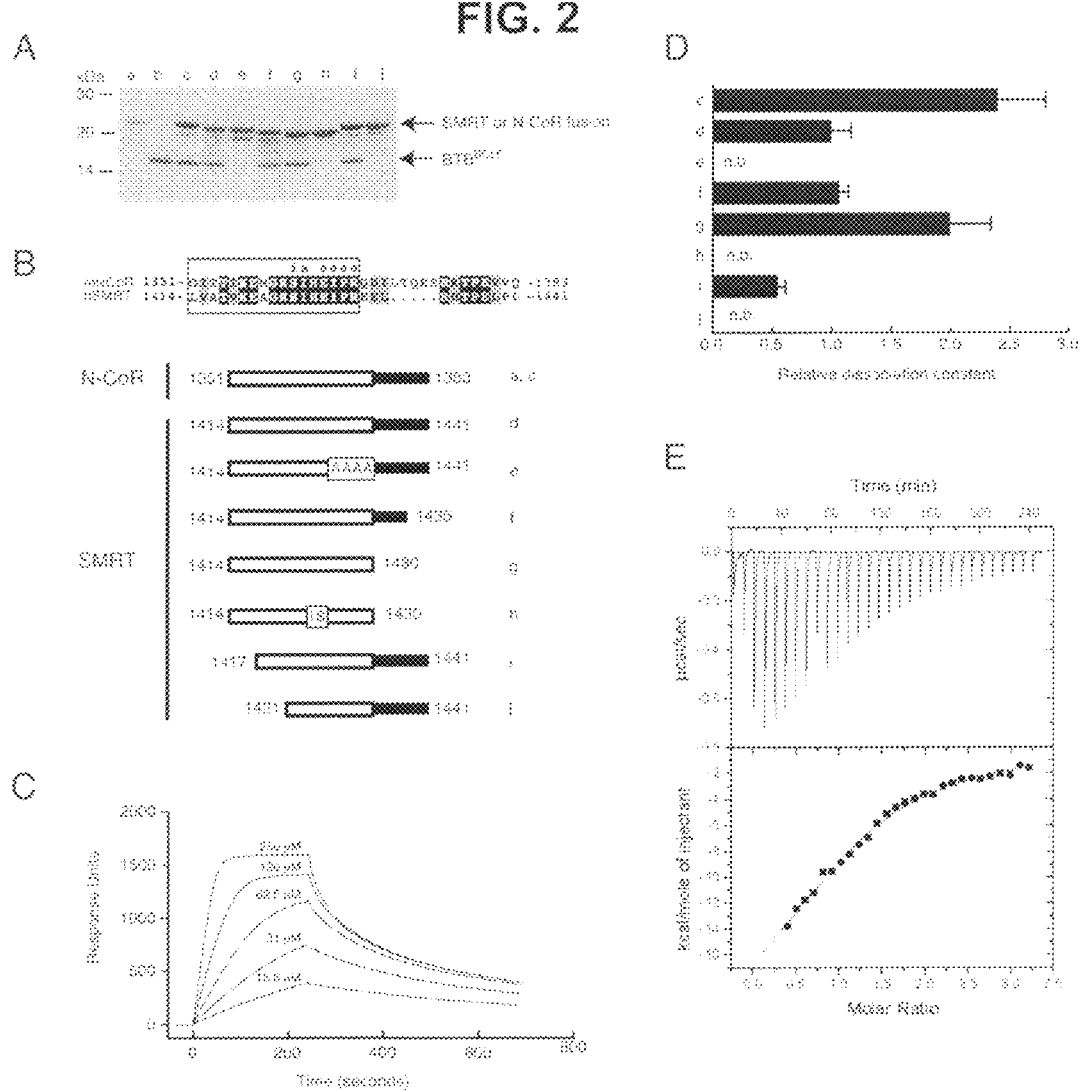
FIG. 2 is a photograph, diagrams and graphs establishing the identification of the minimal BCL6-3C BTB interaction fragment in SMRT. Panel A is a photograph of a stained gel of SMRT or N-CoR fragments expressed as His-tagged thioredoxin (Trx) fusion proteins, purified, and mixed with purified BCL6-3C BTB domain. Complexes were affinity purified over Ni-NTA columns and separated by SDS-PAGE. Lane a: purified Trx-N-CoR$^{1351\text{-}1383}$; lane b: purified BCL6-3C BTB domain; lanes c-j: copurifications of BCL6-3C BTB domain with the His-tagged corepressor fusion proteins described in panel B. Panel B is diagrams showing the "IS" and "AAAA" substitution mutations replacing SMRT residues 1424-1425, and 1427-1430, respectively. The open box represents the minimal binding domain. Panel C is SPR sensograms showing the binding of the BCL6-3C BTB domain at the indicated concentrations to immobilized SMRT$^{1414\text{-}1414}$ peptide (fragment d). Panel D is a graph of relative affinities of the BCL6-3C BTB domain for the corepressor fragments described in panel B. The data are presented as ratios of the dissociation constants relative to SMRT$^{1414\text{-}1414}$ (fragment d), as measured by SPR. "N.b." indicates no detectable binding. Panel E is a graph of ITC titration of SMRT$^{1414\text{-}1430}$ to a solution of BCL6-3C BTB domain.
Figure 3:
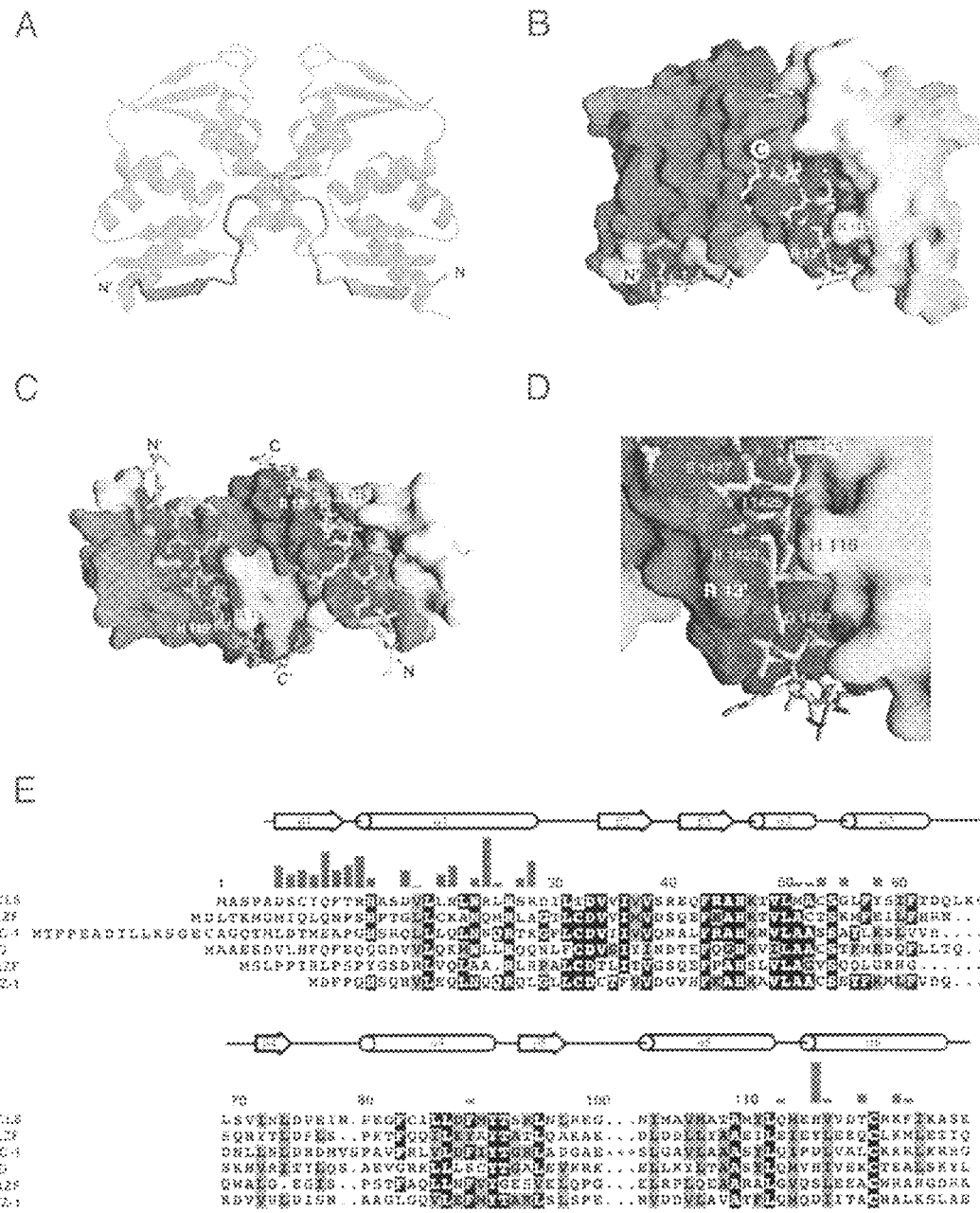
FIG. 3 is diagrams showing the structure of the BCL6-3C BTB domain / SMRT-BBD complex. Panel A is a ribbon diagram of the 2:2 complex. The crystallographic asymmetric unit contains the entire four-chain structure. The N-termini of the two SMRT chains are labeled. Panels B, C and D shows views of the BCL6-3C BTB domain displayed as a solvent accessible surface, with the two SMRT fragments rendered in stick representation. The two non-overlapping surfaces of the BCL6-3C BTB dimer that are buried upon peptide binding are the shaded areas behind the stick representations. Panel B is a view in the same orientation as in panel A. Panel C shows the "bottom" of the complex, viewed along the molecular pseudo-twofold axis. Panel D shows that Ser-1424 (hidden by His-116 in this view) and Ile-1425 of SMRT are buried in a groove formed in part by Arg-13' (α1') and His-116 (α6) from the two chains of the BCL6-3C BTB domain. Panel E shows the sequence alignment of selected human BTB/zinc finger proteins and the observed secondary structure of the BCL6-3C BTB domain. The residue-by-residue surfaces buried due to interactions with the SMRT peptide are indicated with bars. HIC-1 has a 13 amino acid insert at the position indicated by the three asterixes.
Figure 4A:
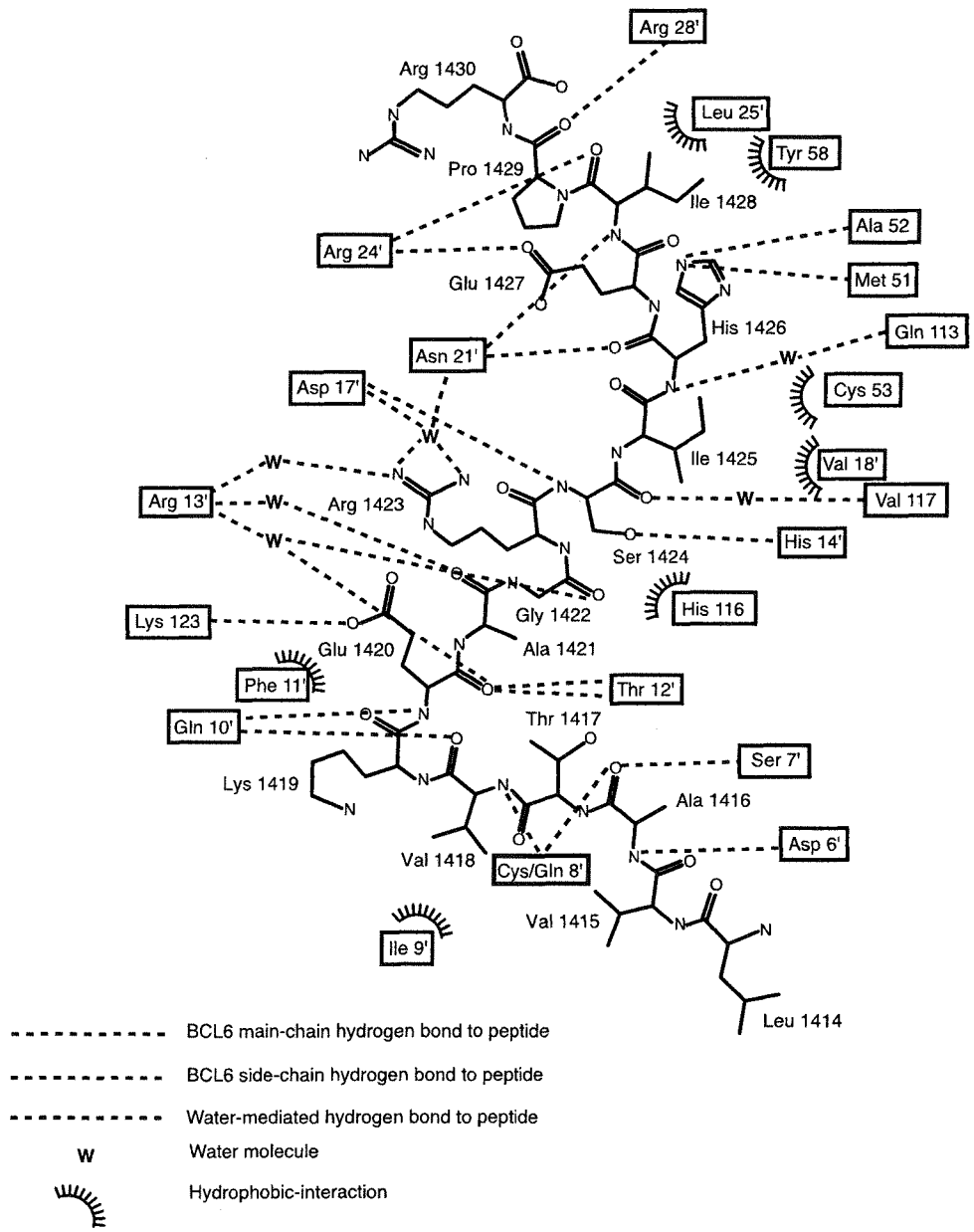
FIG. 4 is illustrations and a photograph showing relevant peptide binding interactions. Panel A shows a schematic drawing of the contacts between the BCL6-3C BTB domain and the SMRT chain. Nearly identical contacts are observed in the other contact surface. Panel B shows a highlight of the interactions between SMRT 1427-1430 and the BCL6-3C BTB domain. Panel C shows interactions of SMRT 1424-1426 with the BCL6-3C BTB domain. In panel D, to view the interactions between region 1414-1423 of the SMRT-BBD peptide and BTB β1', the BCL6-3C helix α6 has been made transparent. Panel E shows the superposition of the two crystallographically independent SMRT peptides from the complex. The six waters from each site that participate in the bridging SMRT/BCL6-3C interactions are indicated as spheres. Panel F is a photograph of a gel showing that mutations in the BCL6-3C BTB peptide binding pocket reduce the affinity for the SMRT peptide. His-tagged Trx-(SMRT-BBD) was mixed with three different forms of the BCL6-3C BTB domain, and the load ("L"), flow through ("FT"), wash ("W") and elute ("E") fractions from each co-purification trial were analyzed by SDS-PAGE.
Figure 4B:
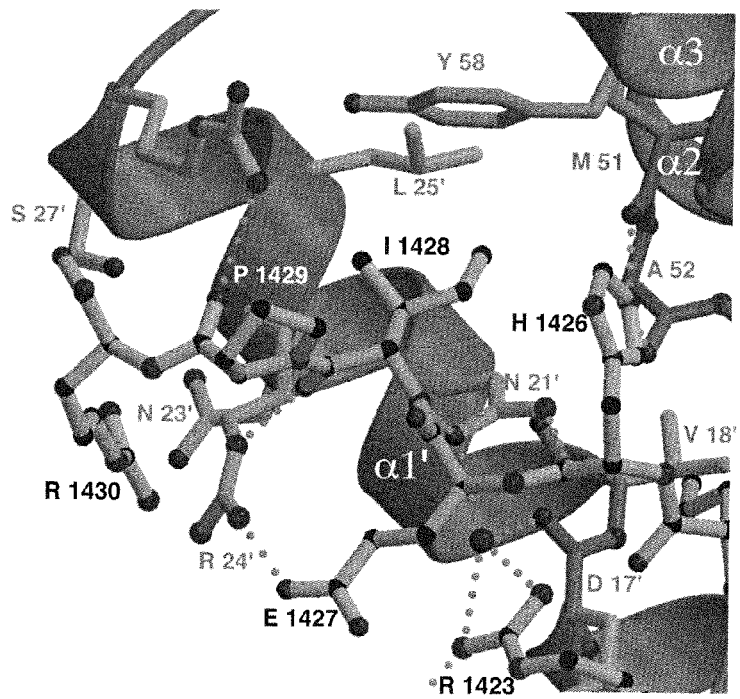
Figure 4C:
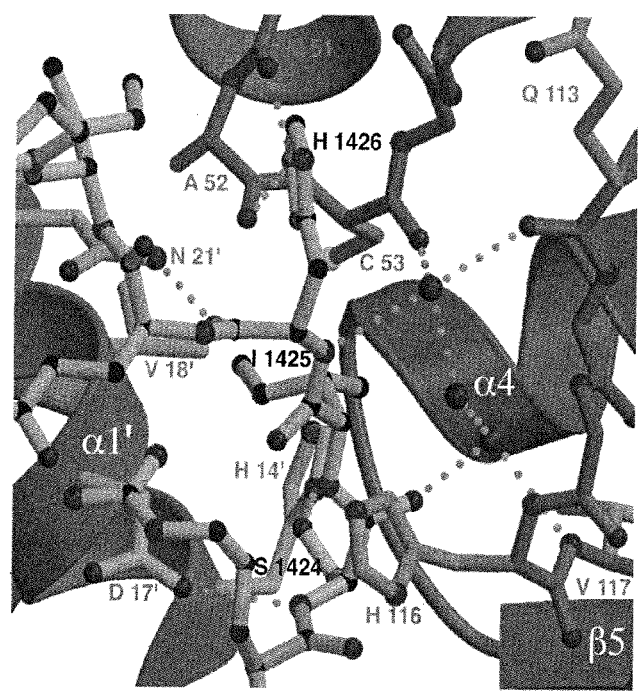
Figure 4D:
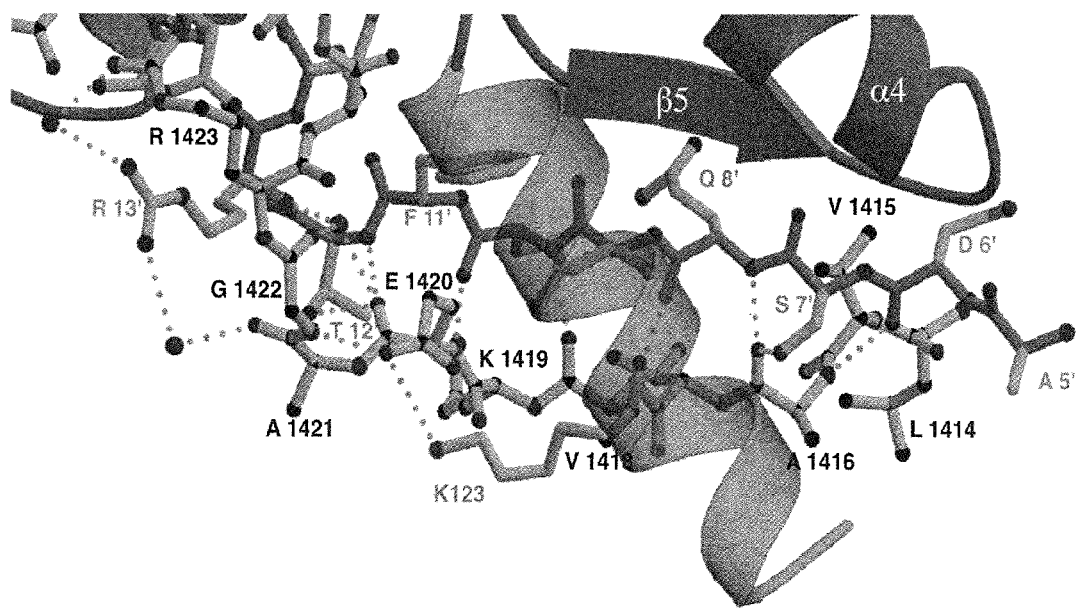
Figure 4E:
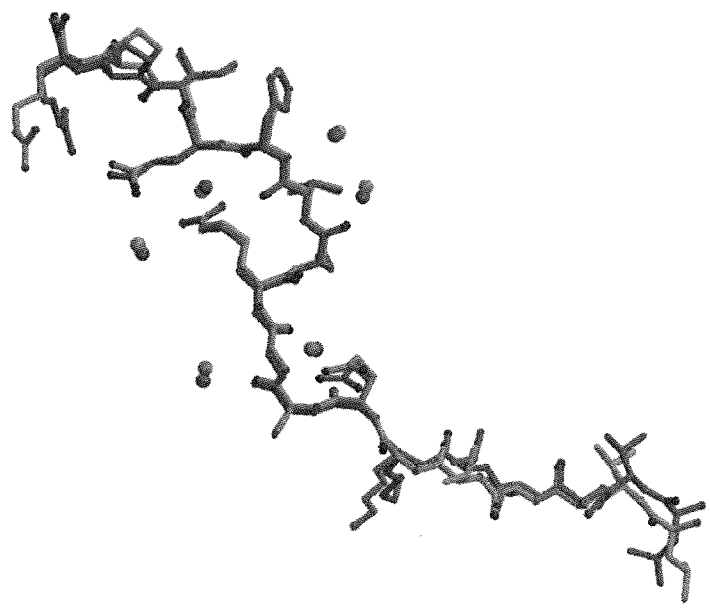

The N-terminal portion of each SMRT peptide interacts in parallel with BCL6 β1, and adds an additional β-strand to the existing β1/β5' sheets at the bottom of the dimer (FIGS. 3 and 4D). The majority of the interactions in this region are mediated by main-chain hydrogen bonds between the peptide and the amino terminus of one of the BCL6 BTB chains. The relevance of these interactions is supported by the binding data, as SMRT residues 1414-1416 make only minor contributions to the strength of the interaction, while the deletion of residues 1414-1420 abrogates complex formation altogether (FIG. 2).

In the middle region of the peptide (FIG. 4C), SMRT residues Ser-1424 and Ile-1425 are deeply buried in the complex, and are found in a groove in the BCL6 BTB domain bounded by Arg-13' (α1') and His-116 (α6). Ser-1424 makes three hydrogen bond interactions to the BCL6 BTB domain, and Ile-1425 points in towards a hydrophobic pocket formed in part by Val-18 (α1') and Cys 53 (α2). As expected, the SI to IS mutation abrogates binding of the SMRT-BBD to the BCL6 BTB domain (FIG. 2), indicating that these residues make critical contributions to complex stability. Surprisingly, BCL6 residues Arg-13 and His-116 make some of the largest contributions to the buried interface surface in the complex, yet they are not conserved within the BTB domain family (FIG. 3E).

A network of polar and non-polar interactions between the C-terminal end of the SMRT peptide and the second half of helix α1 also contribute to the overall stability of the complex (FIG. 4D), although the contacts in this region are not as extensive as in other parts of the interface.

This region is nonetheless required for binding, since replacing residues 1427-1430 of SMRT-BBD with alanines (EIPR->AAAA) abolished the binding as measured by SPR and the copurification assay (FIG. 2). Of these four residues, Ile-1428 makes the most contacts with the dimer.

Figure 4F:
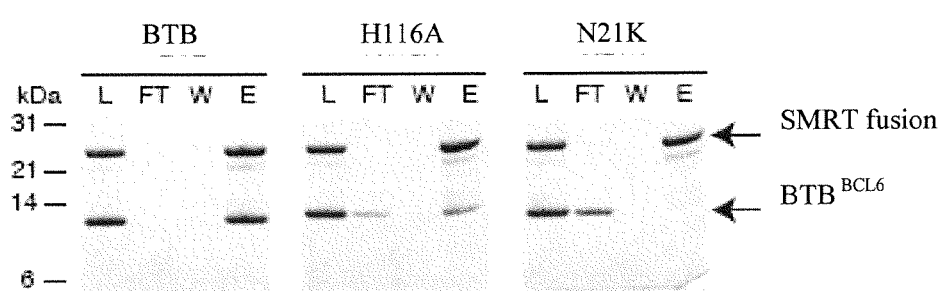

Mutations in the BCL6 BTB domain abrogate the interaction with SMRT-BBD. To further validate the interaction, we mutated BCL6 residues that contact the SMRT peptide. The H116A mutation has a significantly reduced affinity for Trx-(SMRT-BBD), while the N21K mutation showed no binding at all (FIG. 4F). The latter mutant was chosen to introduce the equivalent residue from PLZF into BCL6 (FIG. 3E), and was predicted to be incompatible with SMRT binding based on the observed structure of the complex. The H116A and N21K mutants were well expressed as soluble proteins in *E. coli*, and the purified proteins eluted as single peaks by gel filtration chromatography at similar elution volumes as the native protein. In addition, the two mutant proteins had nearly equivalent CD spectra as the wild type protein, and all three proteins had similar thermal denaturation midpoint transition temperatures (60.2°, 63.1° and 61.0° for the wt, H116A and N21K mutants, respectively). Thus, any differences in the biochemical and biological activity of these mutants are most likely due to changes in the protein-protein interaction properties of the domain, and not due to non-specific effects such as defects in folding (Melnick et al., 2000).

SMRT BBD interacts with the BTB domain of BCL6 but not PLZF in vivo. We next tested whether the interaction of the SMRT-BBD with the BCL6 BTB domain occurred in a similar manner in vivo in mammalian two-hybrid assays. Previous work showed that the interaction of the BCL6 BTB domain with SMRT can be detected in such experiments (Huynh and Bardwell, 1998; Melnick et al., 2002). GAL4-BTB$^{BCL6}$ was co-expressed and allowed to interact with wild-type or mutant VP16-(SMRT-BBD) peptide fusions with substitutions at the critical Ser-1424 and Ile-1425 positions (FIG. 5A). In the absence of the SMRT prey, GAL4-BTB$^{BCL6}$ repressed transcription from the (GAL4)$_5$-TK-Luc containing reporter construct. When VP16-(SMRT-BBD) was co-transfected with GAL4- BTB$^{BCL6}$, the transcriptional response switched from repression to activation, indicating that the two proteins interact. In contrast, both SMRT mutants were unable to mediate activation, indicating weak or no binding to the BTB domain of BCL6. We next performed reciprocal experiments in which GAL4-BTB$^{BCL6}$ wildtype and mutant fusion proteins was used as the bait to capture VP16 activation domain fusions with full-length SMRT (FIG. 5B). The N21K, H116A and N21K/H116A BTB mutants gave background signals indicating no interaction, while the wild-type BCL6 BTB domain produced an activation signal in this assay, indicating that the two proteins interact. Equivalent expression levels of the constructs were verified by immunoblotting (FIG. 5C and D).

We previously reported that the interaction between the PLZF BTB domain and SMRT was undetectable by mammalian two-hybrid assays (Melnick et al., 2002). However, a full-length PLZF GAL4 fusion was able to generate a mammalian two-hybrid signal when co-expressed with full-length VP16-SMRT (FIG. 5E). The interaction was unaffected when SMRT residues 1424 and 1425 were mutated to either AA or IS. In addition, no interaction was observed when VP16-(SMRT-BBD) was used as the PLZF prey. Therefore, the interaction of the SMRT BBD motif described here is specific for BCL6 and not PLZF both in vivo and in vitro. Interestingly, the BCL6 BTB domain is a much more potent transcriptional repressor than the PLZF BTB domain when equivalent amounts of GAL4-BTB expression plasmid are used in reporter assay (FIG. 1 C), correlating with the significantly greater in vitro and in vivo affinity for SMRT.

BCL6 binding to SMRT-BBD directs localization to nuclear speckles. BCL6 normally localizes to nuclear speckles in a BTB-dependent manner (Dhordain et al., 1995). Furthermore, BCL6 and SMRT colocalize in nuclear speckles when overexpressed in transfected cells (Huynh and Bardwell, 1998). Full-length BCL6 could recruit VP16-(SMRT-BBD) to nuclear speckles, while the VP16-(SMRT-BBD$^{SI->AA}$) and VP16-(SMRT-BBD$^{SI->IS}$) mutants showed virtually no spatial overlap with BCL6 (FIG. 5F-N). The BBD motif is therefore sufficient to direct recruitment to BCL6 nuclear speckles in vivo.

Figure 6:
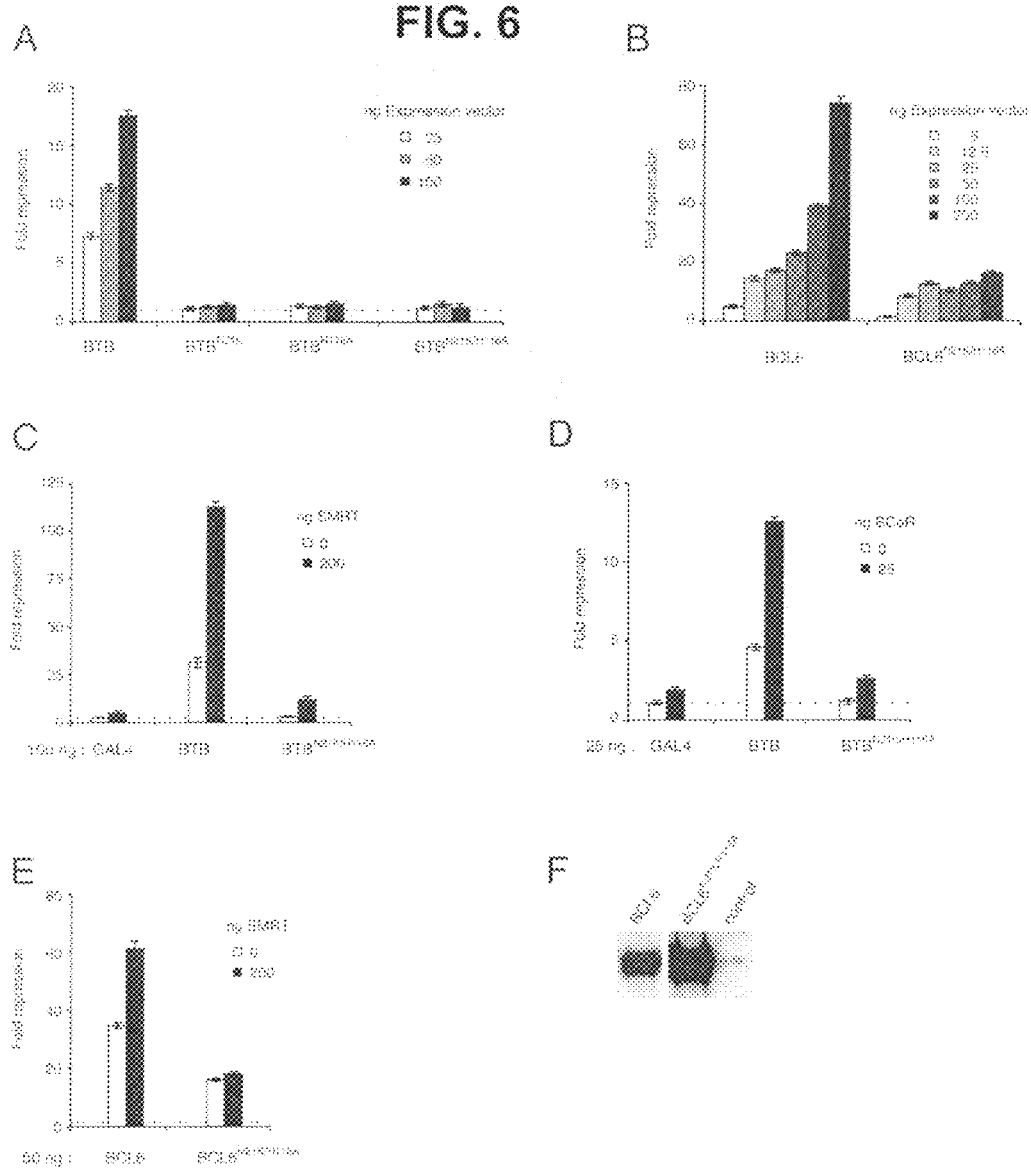
FIG. 6 shows graphs and a photograph showing that the BCL6 BTB/SMRT-BBD interaction is critical for corepressor function. Results are shown as fold repression compared to the relative luciferase units of the empty vector control. Panel A is a graph showing transcriptional repression activity of GAL4-BTB$^{BCL6}$ fusions transfected with a (GAL4)$_5$-TK-Luc reporter construct. Panel B is a graph showing results from reporter assays performed with either full length wild-type BCL6 or full length BCL6 with the N21K/H116A point mutations. The reporter construct ((BCL6)$_4$-TK-LUC) contains four BCL6 binding sites. Panel C is a graph showing corepression of GAL4-BTB$^{BCL6}$ fusions with full-length SMRT. Panel D is a graph showing corepression of GAL4-BTB$^{BCL6}$ fusions with full-length BCoR. Panel E is a graph showing the corepression effect of full-length SMRT with full length BCL6. Panel F shows BCL6 immunoblots of 293T cells transfected with 100 ng of wild-type and mutant full-length BCL6 plasmids. Immunoblots verifying the expression of the GAL4-BTB$^{BCL6}$ fusion proteins are shown in FIG. 5C.

The BTB lateral groove is required for BCL6 transcriptional repression. Since the BCL6 lateral groove appears to the major binding site for BBD containing corepressors, we tested whether this contact was required for transcriptional repression by the BCL6 BTB domain. GAL4-BTB$^{BCL6}$ wild-type or mutant constructs containing the N21K, H116A or N21K/H116A point mutation(s) were co-transfected with a (GAL4)5-TK-Luc reporter. In contrast to wild-type BCL6 BTB, these mutants were completely unable to repress transcription regardless of the dose of expression plasmid administered, suggesting that corepressor binding in this site mediates BTB dependent transcriptional repression (FIG. 6A). When these same mutations were introduced into full-length BCL6, repression activity was greatly reduced, though not abrogated, indicating that motifs in other regions of BCL6 may partially compensate for the defect in BTB corepressor recruitment (FIG. 6B) (Lemercier et al., 2002; Zhang et al., 2001).

The BCL6 BTB lateral groove motif is required for functional interaction with corepressors. Functionally, SMRT, N-CoR and BCoR enhance the levels of repression by BCL6 (Dhordain et al., 1997; Huynh and Bardwell, 1998; Huynh et al., 2000). The interactions between the BCL6 BTB domain and SMRT, N-CoR and BCoR are mutually exclusive (Huynh et al., 2000), and these corepressors presumably compete for a common binding site on the BTB domain. BCoR contains the sequence motif EIPK from residues 481-484, which may be related to the EIPR portion of the SMRT-BBD motif described here. Wild-type and mutant GAL4-BTB$^{BCL6}$ fusion proteins were co-expressed with corepressors in reporter assays. SMRT and BCoR enhanced wild-type BTB repression by 2-3 fold but did not significantly enhance repression by the mutant BTB domains above control levels, indicating that interactions with the BCL6 BTB lateral groove are required for the effect of these corepressors with the BTB domain of BCL6 (FIG. 6C and D).

Finally, to determine whether the BTB lateral groove was also required for corepression of full length BCL6, we tested whether full-length BCL6 harboring the N21K/H116A mutations could functionally interact with SMRT (FIG. 6E and F). While SMRT enhances repression by wild-type full-length BCL6, the protein containing the N21K/H116A mutations is unaffected by the presence of SMRT. Therefore, the lateral groove of the BCL6 BTB domain is required for both physical and functional interaction between BCL6 and BBD-containing corepressors.

Discussion

The BTB domain of BCL6 may have two roles: first, the dimerization and possible oligomerization of the domain is an architectural feature necessary for the normal function of the protein. Second, direct interactions with corepressors are required for the BTB-mediated repression effects. The BCL6 BTB dimer can bind two BBD peptides, and in a biological context, avidity effects may be important for the association of a BCL6 to HDAC complexes that contain two or more SMRT, N-CoR and/or BCoR chains.

Previous observations of dimer-dimer associations between the β1 regions of PLZF BTB dimers (Ahmad et al., 1998; Li et al., 1999) support the suggestion that higher-order BTB complexes may be functionally important (Ball et al., 1999). We observe only one such interaction between BCL6 dimers in the form I and form II structures presented here out of three possible. If similar BTB dimer-dimer associations are important for BCL6 in vivo, it is likely that the association of the SMRT peptide would disrupt these assemblies. Further study will be required to clarify the role, if any, of these effects.

In addition to SMRT, N-CoR and BCoR, the BCL6 BTB domain has been shown to interact with mSin3A and histone deacetylase 1 (David et al., 1998; Dhordain et al., 1998; Wong and Privalsky, 1998), suggesting that several distinct contacts may occur between a BTB domain transcription factor and the components of large repression complexes. While the BTB lateral groove is the site of binding for the BBD motif, additional proteins may recognize other surface features of the domain. The sequences of BTB domains are very diverse (for example, the PLZF and BCL6 BTB domains share only 28% sequence identity), and it is possible that there are additional protein-protein recognition modes in this domain family. Many other protein interaction domains display a wide range of ligand binding properties (Pawson and Nash, 2003). For example, the PH, PTB and EVH1 domains share a common core fold, yet these bind a large variety of peptide or phospholipids ligands using distinct binding sites distributed across the domain surface (Prehoda et al., 1999). In particular, the conserved charged groove at the top of the BTB dimer is a possible protein-protein interaction site (Ahmad et al., 1998; Melnick et al., 2000; Melnick et al., 2002).

The specificity of the SMRT-BBD for the BCL6 BTB domain but not the PLZF BTB domain correlates with the relative strengths of the domains as transcriptional repressors (FIG. 1C; Melnick et al., 2002). An examination of the BCL6 residues that contact the SMRT-BBD peptide provides some insight into the large difference in affinity between the two BTB domains.

Out of the approximately 30 residues of the BCL6 dimer that are buried upon complex formation with SMRT, only three positions (His-14, Asn-23 and Lys-123) are identical in PLZF, while 7 more positions are similar (FIG. 3E). Furthermore, side-chains that make sizable contributions to the buried interface surface in the complex, such as Arg-13, Asn-21, Arg-24, Arg-28 and His-116, are not conserved between the two proteins. An analysis of the corresponding residues in ZID (Bardwell and Treisman, 1994), another transcriptional repressor that recruits components of the histone deacetylase complex (Huynh and Bardwell, 1998), also indicates that the majority of the residues that make sizable contributions to the BCL6/SMRT-BBD complex are not conserved.

The apparent unique specificity of the BCL6 BTB domain for the BBD motif makes this an attractive system for the design of small molecule inhibitors. Recognition of the corepressor motif is essential for the transcriptional repression activity of BCL6, and compounds that disrupt this interaction have potential as therapeutic agents for BCL6-related B-cell lymphoma. Such inhibitors would release the differentiation block in these lymphocytes in a fashion similar to the use of retinoic acid in t(15:17) acute promyelocytic leukemia (APL) (Costoya and Pandolfi, 2001; Lin et al., 2001; Zelent et al., 2001).

Experimental Procedures

Plasmids. Fragments of human BCL6 (codons 5-129), SMRT or N-CoR were subcloned into a modified pET-32 expression vector (Novagen), encoding a thioredoxin fusion protein containing a 6-His tag, a TEV protease site, a BirA biotinylation recognition motif (Cull and Schatz, 2000) and a thrombin protease site N-terminal to the insert site. The GAL4-BTB$^{BCL6}$, BTB$^{PLZF}$ and PLZF mammalian expression vectors, and the (GAL4)$_5$-TK-Luc reporter constructs were previously described (Li et al., 1997; Melnick et al., 2002). VP16-full length SMRT fusions, full-length BCL6 expression plasmid, BCoR expression plasmid and BCL6 binding site reporters were a gift of V. Bardwell (University of Minnesota) (Huynh and Bardwell, 1998; Huynh et al., 2000). Point mutations were introduced using the QuikChange reagents and protocols (Stratagene).

Protein Expression and Purification. Fusion proteins were expressed in *E. coli* BL21(DE3), and were purified by Ni-NTA affinity chromatography (Qiagen) followed by Superdex-75 chromatography (Pharmacia) in 250 mM NaCl, 20 mM Tris-HCl, pH 8.0. BCL6 BTB domain protein was produced by thrombin digestion of the thioredoxin fusion proteins, and repurified by size-exclusion chromatography in 500 mM NaCl, 20 mM Tris-HCl, 10% glycerol, 1.0 mM TCEP, pH 8.5. Corepressor fusion proteins were biotinylated with BirA and digested with TEV protease to yield peptides for SPR analysis with a biotinylated lysine eight amino acids N-terminal to the first corepressor residue, or digested with thrombin to produce peptides with no additional N-terminal residues for co-crystallization or ITC.

In vitro binding assays. Co-purification: Equimolar amounts of His-tagged thioredoxin-corepressor fusion protein and BCL6 BTB or PLZF BTB domain were combined, incubated for at least two hours, and loaded onto a Ni-NTA spin column (Qiagen). The column was washed three times with 600 µl of wash buffer (200 mM NaCl, 20 mM Tris-HCl pH 8.0, 10 mM imidazole), and bound protein was released with 400 µl of elution buffer (200 mM NaCl, 20 mM Tris-HCl pH 8.0, 300 mM imidazole). Samples were analyzed on 10-20% SDS-PAGE gels and stained with Coomassie blue.

SPR: Biotinylated corepressor peptides were coupled to streptavidin-coated sensor chips to a density of 800 response units (Biacore 2000). BCL6 or PLZF BTB protein was serially diluted in running buffer (10 mM Hepes, pH 7.4, 150 mM NaCl, 3 mM EDTA, 0.005% v/v surfactant P20) and injected at a flow rate of 5 µL/min.

ITC: The binding of SMRT$^{1414-1430}$ to BTB domain protein was analyzed on a Microcal VP-ITC instrument at 25° C. All components were in 150 mM NaCl, 20 mM Hepes pH 7.7, 1 mM TCEP. The experiment consisted of thirty 6.93 µL injections of a solution containing 480 µM SMRT$^{1414-1430}$ into a sample cell containing 1.8 mL of either BCL6 BTB (23.0 µM) or PLZF BTB (38.5 µM). To correct for dilution and mixing effects, a series of control injections was carried out, in which the heat of dilution was measured in blank titrations by injecting the peptide into the buffer.

Crystallization and Structure Determination. Form I BTB$^{BCL6}$ : Crystals were grown at room temperature in hanging drops by mixing 2 µL of 8 mg/mL protein with 2 µL of reservoir buffer (0.18 M sodium formate and 0.1 M sodium acetate, pH 4.8). A native dataset to 1.3 Å, and three wavelength anomalous diffraction dataset on selenomethionine-substituted protein to 2.1 Å were collected at 100 K at beamline 14D of the Advanced Photon Source (APS). The data were processed with DENZO (Otwinowski and Minor, 1997). SOLVE was used for locating the selenium atoms and initial phasing (Terwilliger and Berendzen, 1999). Initial model refinement was with CNS (Brunger et al., 1998), and later continued with SHELXL-97 (Scheldrick and Schneider, 1997) on the native dataset.

Form II BTB$^{BCL6}$: Crystals were grown at room temperature in hanging drops by mixing 2 µL of protein with 2 µL of reservoir buffer (30% PEG 8000, 0.18 M Sodium Acetate, 0.1 M HEPES pH 7.0). Data were collected at 100 K on a MAR-345 Imaging Plate Detector on a Rigaku RU200 with a copper target. The structure was solved by molecular replacement (CNS) using the form I BCL6 BTB structure, and refined with CNS.

BTB$^{BCL6}$/SMRT$^{1414-1430}$ complex: Crystals were grown in hanging drops by mixing 2 μL of a protein solution containing 15 mg/mL BCL6 BTB and a 2.5 molar excess of SMRT$^{1414-1430}$ with 2 μL of reservoir buffer (25% PEG 3350 and 0.2 M ammonium acetate). Data collection, structure solution and refinement were as described for the form II crystals. Molecular graphics in FIGS. 1, 3 and 4 were generated with PyMol, Molscript and Raster 3D.

Mammalian two hybrid assays. Assays were performed in 5×10$^5$ 293 T cells plated in 12-well dishes. GAL4 fusion expression "bait" vectors and VP16 "prey" vectors were cotransfected as indicated in the figure legends. Transfections were performed in quadruplicate using the Superfect lipid reagent (Qiagen) and were repeated 4 to 8 times. Cell lysates were subjected to dual luciferase assays (Promega). Equivalent levels of protein expression from the transfected plasmids was verified by immunoblotting with rabbit polyclonal GAL4$^{1-147}$ (sc-577) antibodies or mouse monoclonal VP16 (14-5) antibodies (Santa Cruz).

Immunofluorescence. 293 T cells were transfected with either 100 ng of pEF-BCL6 or pEF vector control with 200 ng VP16-SMRT constructs or VP16 vector plasmid control. Cells were fixed in ice cold methanol, blocked with 10% donkey serum, permeabilized in 0.1% Tween and then exposed to BCL6 D-8 monoclonal antibody (Santa Cruz) and VP16 polyclonal antibody (Clontech). The cells were exposed to donkey anti-mouse secondary antibodies conjugated to Cy2 and donkey anti-rabbit secondary antibodies conjugated to Cy3 (Jackson Immuno-Research, West Grove, Pa.). Vectashield mounting medium with 4', 6'-diamidino-2-phenylindol (DAPI) was then applied (Vector Laboratories, Burlington Calif.). Images were collected using a BioRad Radiance 2000 Laser Scanning Confocal Microscope.

Repression assays. Reporter assays were performed in 293 T cells seeded at a density of 5×10$^5$ cells per well of a twelve well dish. 100 ng of either (GAL4)-TK-Luc and (BCL6)4-TK-Luc reporters were co-transfected with 10 ng of TK-Renilla internal control plasmid using Superfect (Quiagen). Lysates were submitted to dual luciferase assays as per the manufacturer's protocol (Promega). Equivalent levels of protein expression from the transfected plasmids was verified by immunoblotting with rabbit polyclonal GAL4$^{1-147}$ (sc-577) antibodies or mouse monoclonal BCL6 (D8) antibodies (Santa Cruz).

Accession Numbers. The coordinates for the form I, form II and BBD peptide complex crystal structures of the BCL6 BTB domain have been deposited to the Protein Data Bank with accession codes 1R29, 1R28 and 1R2B, respectively.

EXAMPLE 2

Dissecting the BCL6 Repressosome in vivo as Transcription Therapy for B-cell Lymphomas Example Summary The BTB/POZ transcriptional repressor BCL6 is frequently misregulated in B-cell lymphomas. We identified the interface through which the BCL6 BTB domain mediates recruitment of the SMRT, N-CoR and BCoR corepressors. To determine the contribution of this interaction to BCL6 mediated gene silencing and lymphomagenesis we generated specific peptide inhibitors that penetrate cells, bind BCL6 and block corepressor recruitment. These peptides modified the chromatin structure of BCL6 target promoters, abrogated BCL6 mediated repression, reactivated BCL6 target genes, and induced apoptosis and cell cycle arrest in B-cell lymphoma cells. Therefore, SMRT, N-CoR and BCoR play essential roles in BCL6 repression and are required for BCL6 to maintain the malignant phenotype of diffuse large B-cell lymphoma cells. BCL6 BTB blockade may thus constitute a novel form of targeted transcription therapy.

Research Rationale, Results and Discussion

The BTB/POZ domain is a highly conserved ~120 residue polypeptide motif found in over 200 human proteins. A subfamily of BTB proteins contain C-terminal DNA binding motifs (usually C2H2 zinc fingers) and function as transcriptional repressors, several of which are implicated in human cancers including the BCL6, PLZF and Hic-1 proteins. In all of these proteins, the BTB domain is required for transcriptional repression, dimerization, oligomerization, and localization to specific nuclear compartments. We are interested in the mechanisms of action of these transcriptional repressors and the role of the BTB domain in the molecular pathophysiology of human cancer. We previously showed that BTB domains mediate obligate homo-dimerization through a conserved hydrophobic face and oligomerization through a separate hydrophobic surface region. These architectural features are conserved and swappable among BTB proteins and required for their biological functions.

Figures 7A, 7B, 7C:
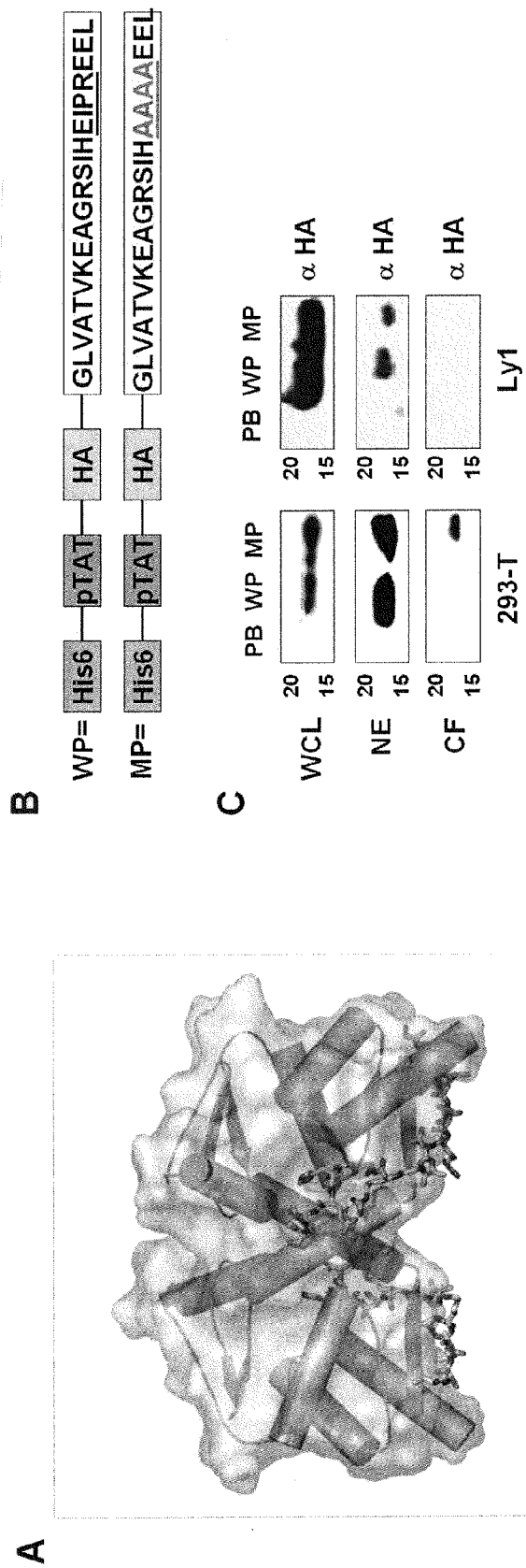
FIG. 7 is diagrams, photographs and micrographs demonstrating that BBD peptides bind to BCL6 and block recruitment of SMRT. Panel A shows a 1.3 Å resolution image of the BCL6 BTB dimer-SMRT BBD complex. The surface of the dimer is shown in white and the peptide backbone of each monomer is shaded. Two BBD sequences (stick representations) bind simultaneously to the BTB dimer. Panel B shows the amino acid sequence of the WP and MP BBD peptides. Panel C shows immunoblots of whole cell lysates (WCL), cytoplasm (CF) and nuclear extract (NE) 293T and Ly1 cells with HA antibodies after a one hour exposure to PB, WP or MP. Panel D shows immunoblots of an in vitro co-immunoprecipitation of endogenous BCL6 with BBD peptides. Ly1 NE exposed to PB, WP or MP (0.12 mg/ml) were precipitated with BCL6 monoclonal antibodies or normal mouse serum (NMS) and immunoblotted with HA antibody. Panel E shows immunoblots of in vivo co-immunoprecipitations of BCL6 and BBD peptides. Ly1 and 293T cells transiently transfected with BCL6 were exposed to PB or 1 µM WP or MP for 1 hour. Immunoprecipitations and immunoblotting were performed on these lysates as in panel D. Panel F shows immunoblots of in vitro co-immunoprecipitations of PLZF and BBD peptides. NE of 293T cells transiently transfected with PLZF were exposed to PB or 1 µM WP or MP for 1 hour. PLZF was immunoprecipitated, and immunoblotting was performed as indicated. Panel G shows immunoblots of in vivo co-immunoprecipitations between BCL6 and SMRT. 293T cells were co-transfected with BCL6 and SMRT and exposed to PB or 1 µM WP or MP for 1 hour. Lysates were subjected to immunoprecipitation with BCL6 rabbit polyclonal antibodies or normal rabbit serum (NRS) and immunoblotted with SMRT polyclonal antibodies. Lysate input expression of SMRT and BCL6 and actin loading controls are also shown. Panel H shows immunofluorescence confocal micrographs of BCL6, SMRT, and BBD peptides. 293T cells were co-transfected with BCL6 and SMRT and after 24 hours were exposed to PB or 1 µM WP or MP for one hour. Immunostaining was performed using mouse BCL6 with and rabbit HA or SMRT and secondary antibodies conjugated with Cy2 (BCL6) or Cy3 (HA or SMRT), followed by DAPI staining, and visualized by laser confocal scanning microscopy. The type of treatment (PB, WP or MP) is indicated to the left of each row of images.

BTB domains also mediate repression through actions specific to each protein. In particular, the BCL6 BTB domain is a potent repressor that directly binds SMRT, N-CoR and BCoR corepressors in a mutually exclusive manner. Mapping experiments indicated that these corepressors bind the BCL6 BTB domain through a conserved 17 residue motif (hereon called "BBD", for BCL6 binding domain). Crystallographic analysis of the BCL6BTB/BBD complex revealed that the BBD directly binds a "lateral groove" motif specific to the BCL6 BTB domain (FIG. 7A). The lateral groove-BBD interaction plays a key role in BCL6 interaction with SMRT, N-CoR and BCoR in vivo and is required for BTB domain-mediated transcriptional repression of reporter constructs.

Transcriptional repression of target genes is the only known action of BCL6, and is attributed in large part to the BTB domain. However, the BCL6 ZnFs participate in repression as well by recruiting the ETO corepressor and class II HDACs and a medial region of BCL6 also has repressor activity. In addition to repression through direct binding to target genes, BCL6 may function as a corepressor for AP-1 in a BTB domain-dependent manner and to reduce GATA-3 protein levels through a post-transcriptional mechanism. The relevance and hierarchy of each of these domains and mechanisms of BCL6 gene regulation are unknown. Finally, little is known of what contributions are made to endogenous transcriptional repression by SMRT/N-CoR and BCoR and how this impacts on the biological actions of their partner transcription factors.

Regulatory elements of the BCL6 gene are frequently mutated in human diffuse large B-cell lymphomas (DLBCL) by chromosomal translocations or somatic hypermutation. This leads to inappropriately timed expression of BCL6, which is otherwise tightly controlled in B-cells. Normally, BCL6 detains antigen-stimulated B-cells in lymphoid follicles to form germinal centers and permits maturation of activated B-cells to high-affinity immunospecific lymphocytes. In lymphomas, sustained BCL6 expression is postulated to favor B-cell proliferation and survival in the face of ongoing mutagenesis by the somatic hypermutation machinery. In spite of intensive studies, and its consideration as a molecular marker of disease prognosis in B-cell lymphomas, it is not known whether BCL6 is required to maintain the malignant phenotype of tumor cells and whether such a role is restricted to cells with mutations in the BCL 6 gene (40% of cases), or to all BCL6 positive B-cell lymphomas (80% of cases).

Since our previous data (Example 1) indicate that the lateral groove-BBD interaction is a critical interface for SMRT/N-CoR/BCoR recruitment to the BCL6 BTB domain, we reasoned that lateral groove blockade offers the unique possibility of determining the contribution of these corepressors to transcriptional and biological actions of BCL6, the contribution of BCL6 repression to its biological actions and, the contribution of BCL6 to the malignant phenotype of different classes of B-cell lymphomas. Finally, were BCL6 to require lateral groove corepressor recruitment for oncogenic effects, blocking reagents would constitute a highly specific and potent form of transcription therapy for human patients with these diseases.

To test this hypothesis, a peptide inhibitor (WP) was designed (FIG. 7B), consisting of four basic elements: an N-terminal (His)6 tag for affinity purification, a protein transduction domain (PTD) from the HW pTAT protein for peptide delivery into the cells (Frankel and Pabo, 1988), a hemagglutinin (HA) epitope tag for immunodetection, and the human SMRT BBD (residues 1414-1430), for specific binding to the BCL6 lateral groove (FIG. 7B). As a negative control a mutant peptide (MP) was engineered where the BBD contained an EIPR->AAAA mutation, which we previously showed (Example 1) abrogates binding to BCL6. These peptides were expressed in E. coli and purified from the insoluble fraction of bacterial lysates.

To verify transduction and intracellular localization, B-cell lymphoma cells (Ly1, Ly4 and Ly8 DLBCL cells, Raji and Daudi Burkitt lymphoma cells) and 293T cells were treated with several different concentrations of purified WP and MP. Whole cell lysates, cytoplasmic and nuclear extracts were obtained and western blots performed with α-HA antibodies to detect the peptides (FIG. 7C). Both WP and MP peptides efficiently penetrated cells and localize preferentially in the nucleus. We previously showed that the BBD binds to BCL6 but not other BTB proteins. To confirm specific binding of our peptides to BCL6, Ly1 nuclear extracts were mixed with peptide buffer (CB), or 1 µM of WP or MP respectively. Ly1 cells are used extensively in these studies, since they are derived from a DLBCL patient with BCL6 gene exon 1 mutations that cause loss of BCL6 autoregulation—and are thus a potentially "BCL6 dependent" tumor.

Figures 7D, 7E, 7F, 7G, 7H:
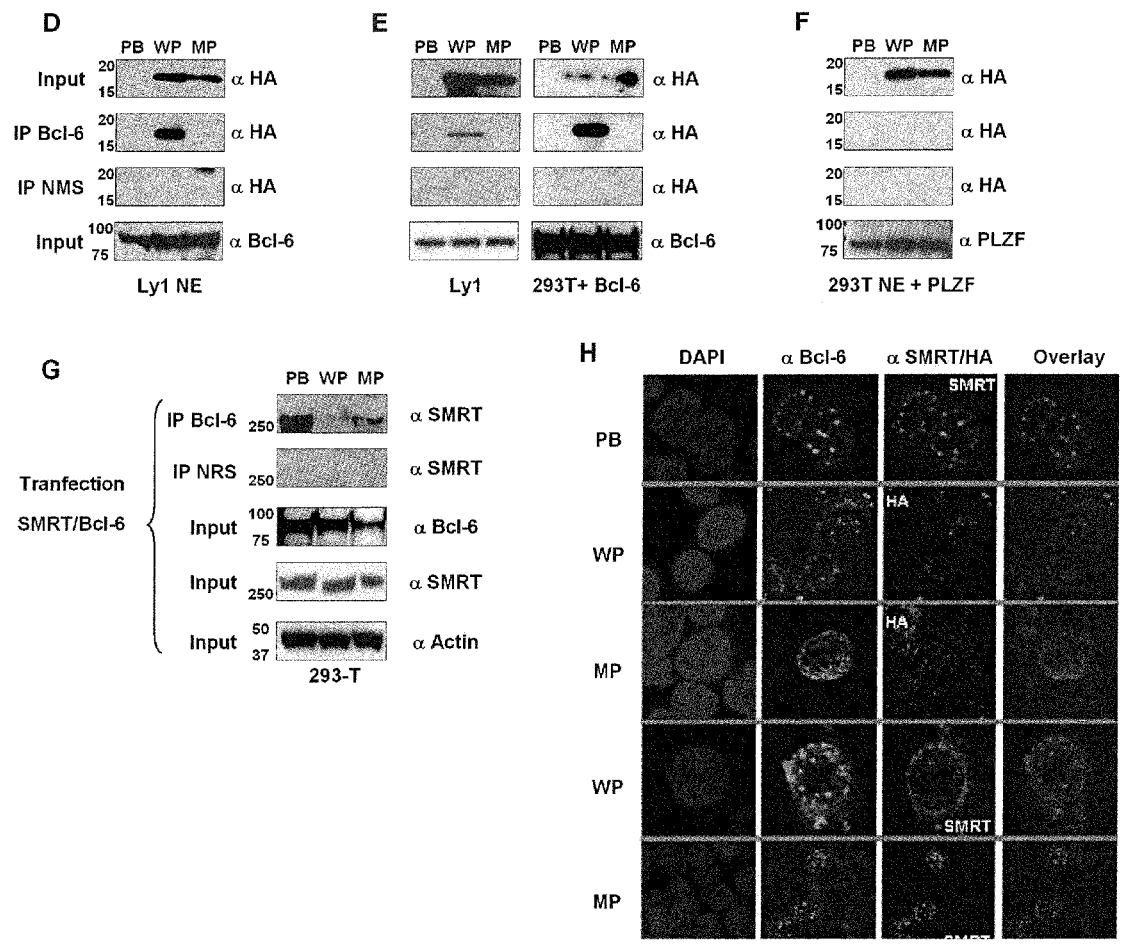

Co-immunoprecipitations (Co-IP) using anti-BCL6 antibodies were performed followed by western blot against the HA epitope of the peptides (FIG. 7D). Consistent with our expectations, WP but not MP interacted with endogenous BCL6 from Ly1 cells. Similar results were obtained using Lysates from 293T cells transfected with full-length BCL6 and exposed to BP or 1 µM WP or MP for one hour (FIG. 7E).

We next determined whether lateral groove binding by WP peptide could displace the SMRT corepressor in vivo. Co-immunoprecipitations between SMRT or N-CoR with BCL6 are challenging with existing antibodies and hence there are no examples of such experiments in the literature. Accordingly, we found that coimmunoprecipitation of BCL6 with endogenous corepressors cells was elusive since these proteins are expressed at low levels. However, by extensive optimization we obtained reproducible co-immunoprecipitations between BCL6 and SMRT in transfected 293T cells. Forty-eight hours after transfection, the cells were exposed to either PB, or 1 µM WP or MP for one hour. Remarkably, the WP peptide consistently abrogated SMRT binding to BCL6, whereas the mutant peptide failed to do so (FIG. 7F). BCL6 normally localizes in nuclear speckles, where it colocalizes with SMRT. By transfecting low levels of BCL6 and SMRT in 293T cells we were able to reproduce the endogenous staining pattern of BCL6 and SMRT. The impact of lateral groove blockade on BCL6-SMRT colocalization was determined by exposing these cells to PB, WP or MP as described above. Cells were then co-stained for BCL6 and SMRT or BCL6 and HA and visualized in sections by confocal microscopy (FIG. 7G). We found that BCL6 and SMRT colocalization occurred in the presence of PB or 1 µM MP, but was disrupted in presence of 1 µM WP. Reciprocally, BCL6 colocalized with WP but not MP, indicating that WP peptide binding was mutually exclusive with corepressor binding, and that the BTB lateral groove contact site is necessary and sufficient for SMRT binding to BCL6 in vivo. Furthermore, structure guided design of blocking molecules can lead to production of effective inhibitors of transcription factor-corepressor interactions proteins.

Figure 8:
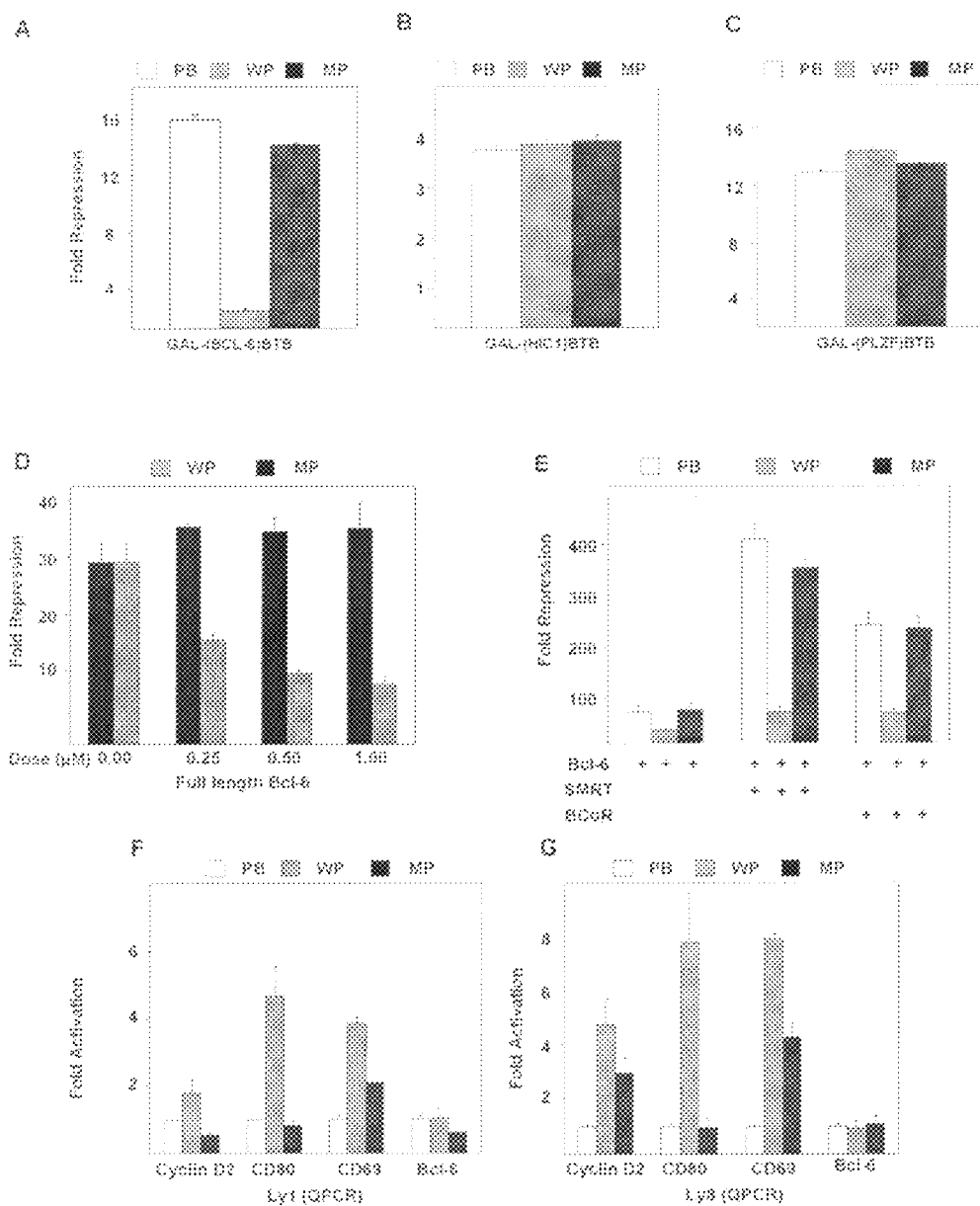
FIG. 8 is graphs demonstrating that lateral groove corepressor blockade is specific for BCL6 and is required for transcriptional repression of natural and endogenous target genes. Panels A-E shows results of reporter assays performed in 293T cells transfected with constructs as indicated and TK-renilla as internal control. In all cases, after 24 hours cells were exposed to PB (white bars), or 1 µM WP (gray bars) or MP (black bars) for 20 hrs and harvested for dual luciferase assays. Fold repression is calculated compared to BCL6. Fold repression was calculated relative to vector control for each experiment. Transfections were performed in 24-well dishes as follows: Panel A: 50 ng of GAL4$^{1-147}$ or GAL4-BCL6$^{BTB}$ with 50 ng (GAL4)$_5$_TK-Luc reporter; Panel B: 50 ng of GAL4$^{1-147}$ or GAL4-HIC1$^{BTB}$ with 50 ng (GAL4)$_5$_TK-Luc reporter; Panel C: 200 ng GAL4$^{1-147}$ or GAL-PLZF$^{BTB}$ with 50 ng (GAL4)$_5$_TK-Luc reporter; Panel D: 50 ng of pEF vector or full length pEF-BCL6 with 50 ng (BCL6)$_3$_TK-Luc reporter; Panel E: 50 ng of pEF vector or full length pEF-BCL6 with 50 ng (BCL6)$_3$_TK-Luc reporter alone or with 200 ng of CMX-SMRT or 200 ng pEF-BCoR. Panel F shows the results of real time PCR detection of mRNA of the endogenous BCL6 target genes cyclinD2, CD80, CD69 BCL6, performed in Ly1 and LY8 cells, treated with PB (white bars), or 1 µM WP (gray bars) or MP (black bars) for 7 hours.

Our previous data indicate that lateral groove point mutations disrupt transcriptional repression by the BCL6 BTB domain, consistent with loss of corepressor recruitment. We reasoned that since WP peptides block SMRT binding to BCL6, BTB domain-mediated transcription would be impaired. To determine whether this is the case, 293T cells were transfected with a GAL4-BCL6$^{BTB}$ fusion expression vector and a GAL4 responsive reporter construct and an internal control reporter. Twenty four hours after transfection, cells were exposed to PB, WP, MP or nothing over the next 20 hours. Remarkably, WP but not MP or PB abrogated BCL6 BTB domain transcriptional repression (FIG. 8A). Growth and viability of 293T cells was unaffected by any of these reagents and the protein levels of GAL4BCL6$^{BTB}$ fusions was equivalent in all samples (data not shown).

Other BTB domains autonomously repress transcription, yet none appear to contain lateral groove motifs. For example, the PLZF BTB domain also directly interacts with and requires SMRT and N-CoR, though interaction seems to occur through a distinct charged pocket motif, while the HIC-1 BTB domain also mediates repression but does not interact with SMRT or N-CoR. Therefore, transcriptional repression by these BTB domains should not be affected by the WP peptide. Accordingly, in contrast to BCL6, transcriptional repression by the GAL4-PLZF$^{BTB}$ or GAL4-HIC1 proteins were unaffected by WP or negative controls (FIG. 8A). These results suggest that the lateral groove—BBD mechanism is specific to BCL6 and not other BTB proteins, consistent with our bio-informatic predictions.

We next wished to determine the hierarchy of the lateral groove mechanism, i.e. the contribution of the BBD corepressors, to transcriptional repression by full-length BCL6. Full length BCL6 was expressed together with a (BCL6)$_3$ binding site-TK-Luc reporter and then exposed to increasing doses of WP or MP peptides (250 nM, 500 nM and 1 µM) followed by peptide treatment as above. WP but not MP caused a dose-dependent reduction of BCL6 transcriptional repression, but did not completely abrogate it (FIG. 8B), suggesting that the remaining BCL6 domains mediate residual repression independent of SMRT/N-CoR/BCoR. Alternatively, loss of BCL6 repression may be underestimated by the lag time between transfection and peptide exposure. Finally, the SMRT/N-CoR/BCoR corepressors normally enhance transcriptional repression by BCL6 in reporter assays. Not surprisingly, lateral groove blockade with WP inhibits enhancement of BCL6 repression by BCoR and SMRT (FIG. 8C).

Transcriptional regulation differs in episomal reporter genes vs. the structured chromatin context of endogenous gene loci. The most significant measure of lateral groove effect is thus whether peptide blockade of endogenous BCL6 re-activates endogenous direct BCL6 target genes. We exposed three DLBCL cell lines: Ly1 (mutated BCL6 exon 1), Ly8 (BCL6 translocation), Ly4 (Non mutated BCL6 locus) to buffer, or 1 µM WP or MP for 6 hours, extracted mRNA and performed real time PCR on BCL6 target genes. WP peptide re-activated BCL6 target genes such as CD80 5-8 fold and cyclinD2 2-4 fold in Ly1 and Ly8 cells, whereas there was no effect in Ly4 cells (FIG. 8D). In contrast, MP had little effect on BCL6 target gene expression. Although BCL6 autoregulates its own expression, there was no detectable re-activation in these lymphoma cells, most likely since Ly1 and Ly8 have lost the BCL6 regulatory elements in the mutated alleles. These studies offer direct evidence that the BBD proteins function as corepressors in vivo, and their interaction with the BTB domain is required to maintain silencing by the endogenous BCL6 protein.

Figure 9:
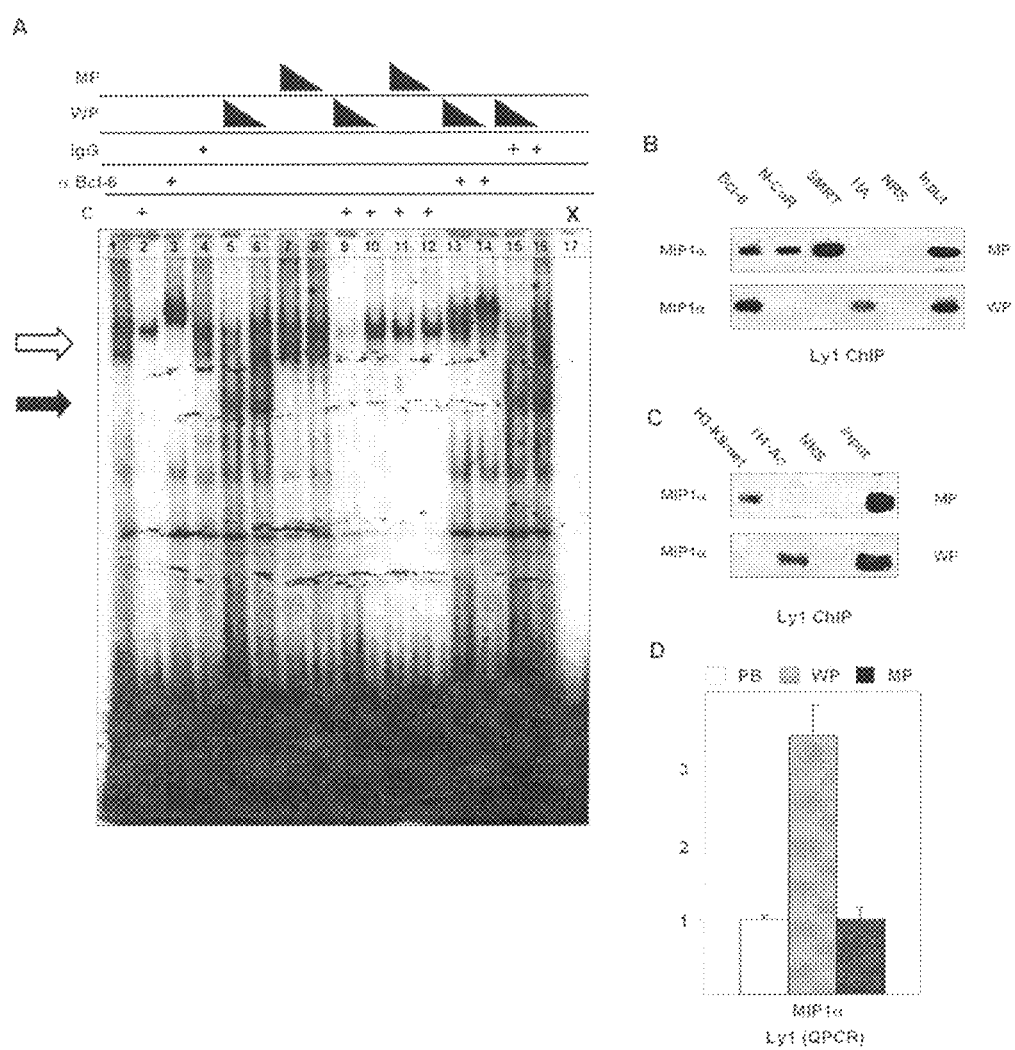
FIG. 9 is photographs of experimental results demonstrating that lateral groove blockade alters BCL6 target promoter repressosome composition and chromatin structure without disrupting DNA binding by BCL6. Panel A shows the results of electrophoretic mobility shift assays performed using nuclear extracts prepared from 293T cells transfected with full length BCL6. In each case 2 µg of nuclear extract was allowed to interact with 10 fmol$^{32}$P labeled oligonucleotides probes containing a canonical BCL6 DNA binding site. In addition, reactions were exposed to 50-fold excess unlabeled probe in lanes 2, 9, 10, 11 and 12; 0.2 µg BCL6 antibody and in lanes 3, 13 and 14, 0.1 µg serum, 5 µg WP in lanes 5, 9, 13 and 15; 1 µg WP in lanes 6, 10, 14 and 16; 5 µg MP in lanes 7 and 11; 1 µg MP in lanes 8 and 12; "X" denotes probe alone in lane 17. White arrow: high molecular weight BCL6 mobility shift. Black arrow: lower molecular weight BCL6 mobility shift in the presence of WP. Panel B shows the results of chromatin immunoprecipitations (ChIP) performed in Ly1 cells treated for 7 hrs with 1 µM of MP or WP. Cross-linked chromatin was precipitated with BCL6, N-CoR, SMRT or HA polyclonal antibodies or normal rabbit serum (NRS). The resulting purified DNA fragments-and 5% input were amplified by end-point PCR using primers surrounding the BCL6 binding site on the MIP-1α promoter. Panel C shows the results of ChIP assays where Ly1 cells were treated as above, but precipitated with histone 3, lysine 9-dimethyl (H3K9-met) or histone 4 pan-acetylated (H4-Ac) polyclonal antibodies or NRS. The resulting purified DNA fragments and 5% input MIP-1α promoter. Panel D shows the results of real time PCR detection of mRNA of the endogenous BCL6 target gene MIP1α, performed in Ly1 cells treated with PB (white bars) or 1 µM WP (gray bars) or MP (black bars) for 7 hours.

To determine whether the effects of WP peptide on repression might be caused by interfering with BCL6 binding to DNA, we next performed electrophoretic mobility assays. Nuclear extracts of transfected 293T cells were allowed to bind radiolabeled oligonucleotides containing either one or three BCL6 binding sites. Different concentrations of WP or MP were added to the reaction and unlabeled DNA probe, anti-BCL6 antibodies or control IgG were used to verify the specificity of the observed complexes. Interestingly, addition of WP caused a dose dependent reduction in the main BCL6-DNA complex in favor of a faster migrating specific complex, with no apparent reduction in overall DNA binding. Furthermore, DNA binding by the BCL6 zinc finger only constructs was unaffected by WP or MP peptides, nor was there any change in the size of the DNA-protein complex (not shown). Results with the single or triple binding site probe were identical, and only the former is shown in FIG. 9A. The same result was seen in nuclear extracts with endogenous BCL6 from Ly1 cells (data not shown).

Disruption of the high molecular weight complex by lateral groove blockade is likely due to loss of BBD corepressors from the BCL6 complex. However, attempts to supershift SMRT and N-CoR from these high molecular weight complexes were unsuccessful (consistent with the experience of other investigators) with the available antibodies. Furthermore, from the physiological standpoint the relevant BCL6 complexes in transcriptional repression are those that form on the promoters of endogenous BCL6 target genes. Endogenous complexes were analyzed by chromatin immunoprecipitations (ChIPs) in the BCL6 positive Ly1 and Ly8 cells after one-hour exposure to WP, MP or buffer. The cross-linked chromatin was pulled down with antibodies against BCL6, SMRT, N-CoR and HA (for the peptide). PCR was performed on the purified DNA using specific primers for BCL6 binding sites of the MIPla promoter, which we have used previously to map BCL6 recruited proteins by ChIPs (FIG. 9B). BCL6 itself bound the MIP1α promoter in the presence of both WP and MP peptides, confirming that lateral groove blockade does not interfere with binding to target genes. In contrast, SMRT and N-CoR were both excluded from the MIPla promoter in the presence of WP but not MP peptide. Finally, the WP but not MP peptide was associated with the MIP1α promoter by ChIPs consistent with its binding to the BTB domain and displacing corepressors. These results indicate that endogenous BCL6 repressosome formation includes the SMRT and N-CoR proteins and that this complex is disrupted by lateral groove blockade.

Transcriptional repressors recruit corepressors to mediate changes in chromatin structure that lead to silencing of the targeted locus. Two such modifications associated with silencing include deacetylation of histone tails and the methylation of lysine 9 of the tail of histone 3. Accordingly, the SMRT corepressor is directly implicate in histone deacetylation. ChIP assays performed in Ly1 and Ly8 cells on the MIPla promoter indicate that histone 4 tails are deacetylated at baseline but become acetylated in the presence of WP peptide, indicating that BBD corepressors mediate deacetylation of histones by BCL6. We also found that BCL6 target genes were methylated on lysine 9 of histone 3. Although a connection between SMRT/N-CoR and histone methylation has not yet been reported, we found that these corepressors were also required for H3-K9 methylation by BCL6. These results suggest that these very large BBD corepressors repress transcription of BCL6 target genes by acting as a scaffold for histone deacetylases and histone methyltransferases. Loss of this scaffold through lateral groove blockade leads to erasure of these chromatin modifications with consequent target gene reactivation.

BCL6 is the most commonly mutated gene in B-cell lymphoma, based on which it is widely implicated as a potential oncogene. This view is supported by the identity of certain BCL6 target genes involved in cell cycle control, apoptosis and differentiation. We reasoned that if BCL6 repression is oncogenic, re-activation of target genes by lateral groove blockade might profoundly alter the phenotype of lymphoma cells. Tumors most likely to respond to WP peptides are those derived from patients with activating mutations in the BCL6 gene, which are presumably BCL6-dependent and include 40% of DLBCL cases, 16% of follicular lymphoma cases, and a significant percentage of AIDS-related lymphomas. In contrast, B-cell lymphomas that express BCL6 but do not have mutations, or that do not express BCL6 might not be BCL6 dependent.

To determine if this is case, the biological effects of lateral groove inhibition were tested in the following DLBCL cells: Ly1 and Ly8 (BCL6 mutated), Ly4 (BCL6 negative), Ly7 (BCL6 positive-not mutated), Ly10 (activated B cell type DLBCL); Germinal center Burkitt Lymphoma Daudi and Raji Cells (BCL6 positive - not mutated), Ly12 cells (T-cell lymphoma - low BCL6 expression) and U937 monocytic leukemia cells. Lymphoma cells were treated for 48 hours with peptide buffer or 1 µM WP or MP peptides and the effects of these treatments on survival, cell cycle and differentiation analyzed.

Figures 10A, 10B:
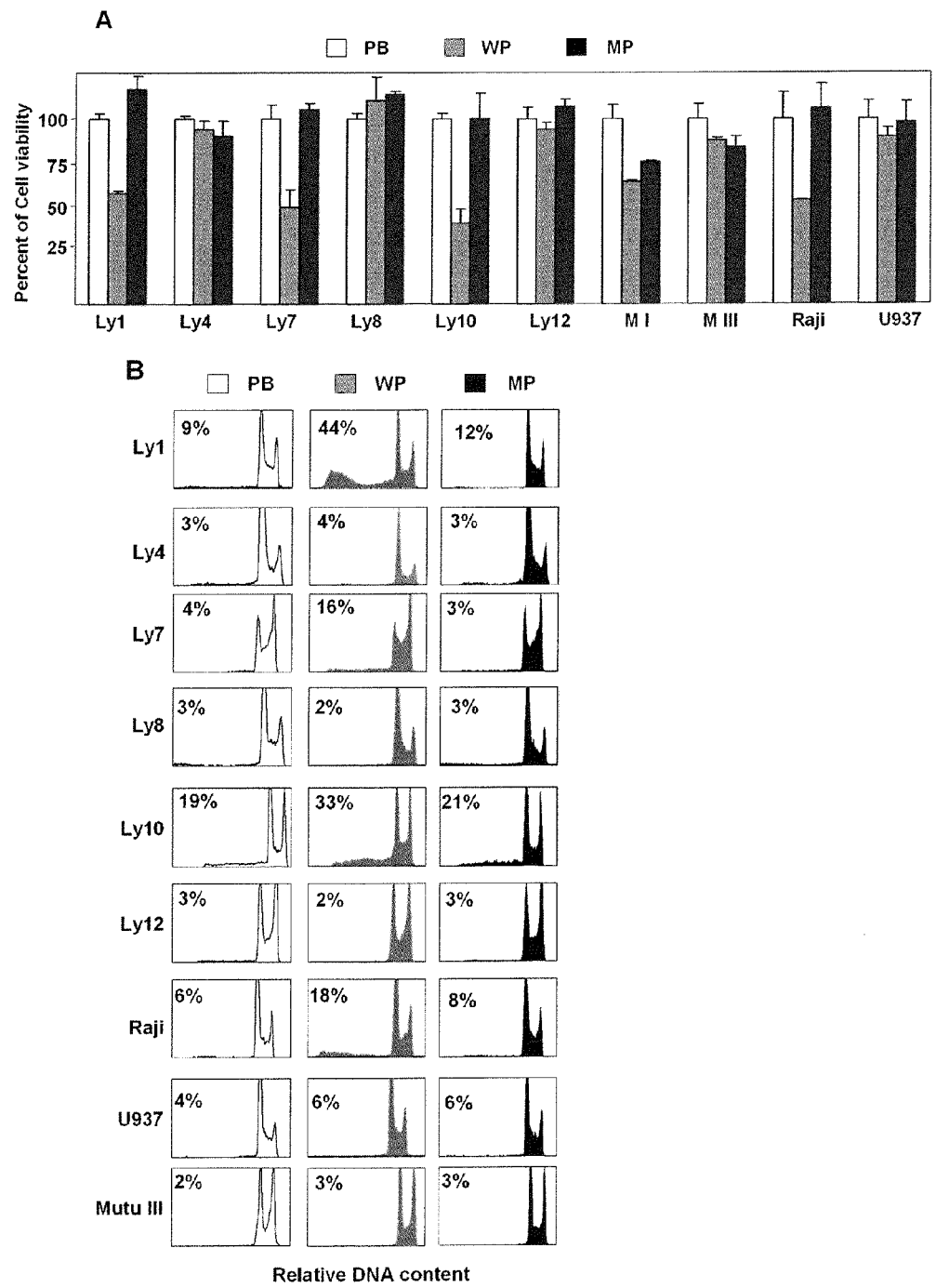
FIG. 10 is graphs and diagrams demonstrating that BCL6 lateral groove blockade causes apoptosis and cell cycle arrest of BCL6 dependent human B-cell lymphoma cells. Panels A-D shows the results of experiments where a group of cells including Ly1, Ly4, Ly7, Ly8, Ly10, Ly12, Raji, Daudi and U937 were exposed to PB or 1 mM WP or MP for 48 hours and evaluated as follows: Panel A: cell viability was determined by performing XTT assays. The results are expressed relative to the viability of cells exposed to buffer alone (which is equivalent to untreated cells); Panel B: apoptosis was determined by FACS counting of fixed cells and stained with propidium iodide. The fraction of apoptotic hypodiploid DNA content (Pre-G1/G0) cells is indicated in each graph; Panel C: Differentiation was determined by staining treated cells with antibodies for the CD10 (germinal center) and CD38 (plasmacytic) surface antigens and performing flow cytometry as indicated; Panel D: Cell cycle progression was determined by fixing and staining cells with propidium iodide and determining DNA content by FACS. Cell cycle analysis was performed using MotFit software.
Figure 10C:
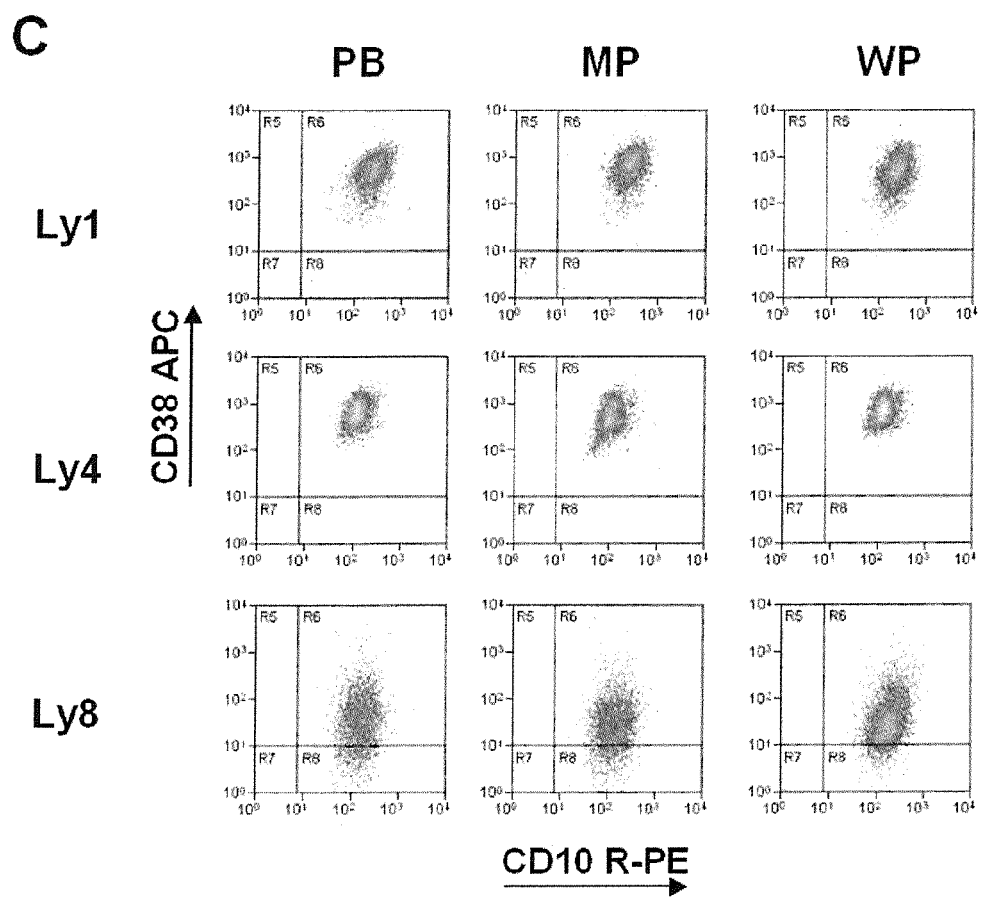
Figure 10D:
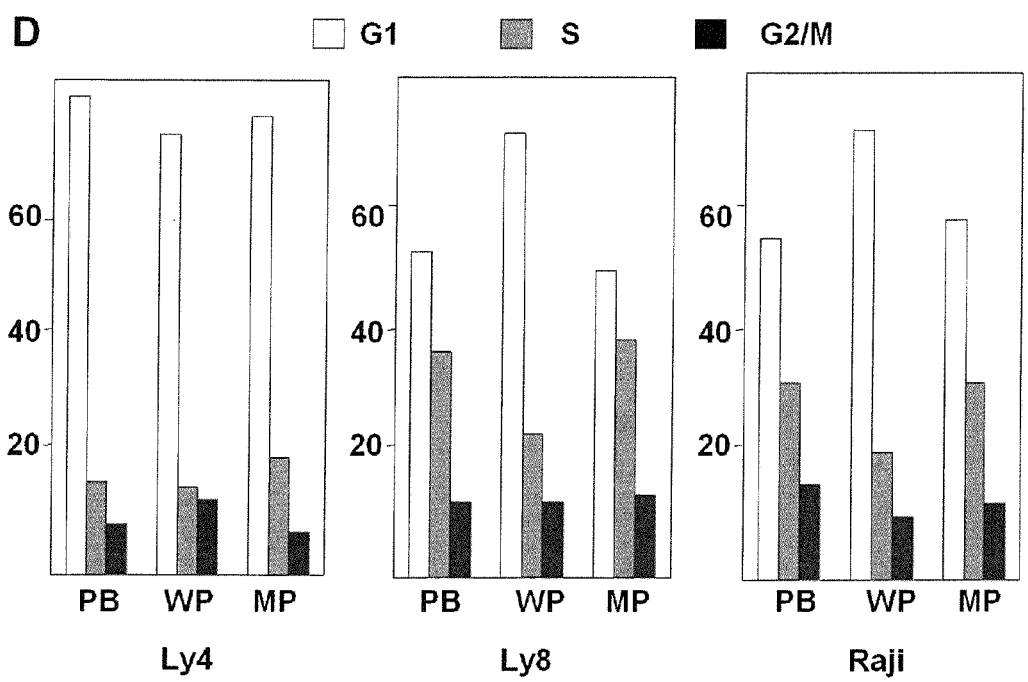

Apoptosis was measured by sub G1/G0 population scoring and Annexin V staining. Remarkably, within 48 hours, 40-50% of the Ly1 cells underwent programmed cell death with WP but not MP or PB. Furthermore, flow cytometry of propidium iodide stained Ly 1 cells of WP indicated that a minority of cells were still viable (FIG. 10A). In contrast, the predicted non-BCL6 dependent cell lines were not affected by peptide treatment, with the exception of Raji cells (20% apoptosis with WP). This result is consistent with Shaffer et al (2000) where a BCL6 zinc fingers- estrogen receptor activation domain fusion protein caused mild apoptosis, and may indicate that BCL6 may participate in maintaining the malignant phenotype in a subset of tumors where the gene is wild type. Similar results were obtained in XTT metabolic viability assays (10B). Cell cycle analysis was performed by propidium iodide staining followed by flow cytometry (FIG. 10C). WP but not mutant peptide induced G1 arrest in Ly1, Ly8 and Raji cells but not in the other cells. These results show that BCL6 is necessary to maintain the malignant phenotype of this kind of B-cell lymphomas. BCL6 is hypothesized to block differentiation of B-cells by repressing the Blimp-1 master regulator of plasma cell differentiation. Our flow cytometry analysis of differentiation markers CD10, CD38 and CD138 indicate that lateral groove blockade does not induce differentiation in any of the B-cell lines analyzed (FIG. 10D). This indicates that either BCL6 is not involved in blocking differentiation, or that putative BCL6 target genes involved in differentiation are not regulated by BBD corepressor recruitment. Taken together, these results suggest that BCL6 expression is required for survival and proliferation of B-cell lymphomas containing BCL6 activating mutations, and may play a role in a subset of non-mutated B-cell lymphomas.

Transcriptional repression occurs through the coordinated actions of protein complexes recruited to specific target genes by sequence specific transcription factors. The composition of these repressosomes may vary from locus to locus, suggesting that different cofactors are involved in regulating different sets of target genes. The specific set of protein-protein interactions that occur in these repressosomes determine the transcriptional outcome as detected by changes in chromatin structure and mRNA expression. We designed a peptide reagent, able to specifically and "cleanly" subtract the contribution of the SMRT/N-CoR/BCoR corepressors from the transcriptional actions of the BCL6 protein. Our results offer direct evidence of the role of these corepressors in endogenous target gene chromatin modification, endogenous transcriptional regulation, and in transcription factor specific biological effects. The fact that lateral groove blockade uncovered the requirement of BCL6 transcriptional repression for survival of DLBCL cells with BCL6 mutations suggest that BCL6 is truly a lymphoma oncogene and not just a marker of cells that have traversed germinal center differentiation.

Finally, in experimental cancer therapy, much attention has been focused on therapeutic re-expression of silenced genes (transcription therapy) with a particular emphasis on the development of drugs that inhibit enzymatic activities, such as histone deacetylase inhibitors. However, the most successful transcription therapy drug is also the only one that directly targets the interaction of a transcriptional repressor with its partner corepressors—i.e. all trans retinoic acid targeting of the PML/RARα oncoprotein in acute promyelocytic leukemia. Similarly, our results suggest that our lateral groove blocking peptide drug is a novel and promising structure guided specific transcription therapy agent. Therefore, we have initiated pre-clinical studies with chemical derivatives with the intent to move into clinical trials in patients with DLBCL.

Materials and Methods

Expression and purification of peptides. The (His)6-pTAT-HA bacterial expression plasmid were obtained from Dr. Steve Dowdy (UCSD). Oligonucleotides containing the wild type (5'-CATGGCTGGTGGCCACGGTGAAGGAG-GCGGGCCGCTCCATCCATGAGATCCCGCGCG AGGAGCTGCGGCACACGCCCGAGCTGC-CCCTGGCCC-3' and 5'-TCGAGGGCCAGGGGCAG CTCGGGCGTGTGCCGCAGCTC-CTCGCGCGGGATCTCATGG ATGGAGCGGCCCGC-CTCCTTCACCGTGGCCACCAGC-3') or mutant BBD (5'-CATGGCTGGTGGCCACGGTGAAGGAGGCGGGCCG CTCCATCC ATGCAGCTGCAGCTGAGGAGCTGCG-GCACACGCCCGAGCTGCCCCTGGCCC-3' and 5'-TC-GAGGGCCAGGGGCAGCTCGGGCGTGTGCCGCAG CTCCTCAGCTGCAGCTGCATGGATGGAGCGGC-CCGCCTCCTTCACCGTGGCCACCAGC-3') BBD sequences were inserted into Nco I and XhoI sites, and the construct verified by automated sequence (Albert Einstein Sequencing Facility). Peptide expression was induced with IPTG in BL21 (D3) E. coli cells (Novagen), which were harvested by centrifugation, washed with PBS and resuspended in lysis buffer (50 mM Tris-HCl pH8, 150 mM NaCl, 5% Glycerol). Lysozyme (1 mg/ml) was added and incubated for 30 min at 4° C. followed by sonication using a Vibra Cell sonicator (Sonic & Material Inc). The sample was centrifuged at 12000 rpm in a Sorvall RCSB centrifuge, and resuspended in a peptide buffer (PB=20 mM Phosphate pH=7.4 10 mM imidazole, 150 mM NaCl, 5% Glycerol, 4 M urea) and affinity purified by Ni-NTA Hi-Trap column (Pharmacia Biotech) using an AKTA Purifier 10 (AP Biotech). The purity of peptide fractions was verified by 15% tricine SDS-PAGE followed by Coomassie Blue staining (Bio-Rad) or by Western Blot using HA polyclonal antibodies (Sigma).

Peptide transduction. Cells were exposed to different concentrations (100 nM, 250 nM, 500 nM, 1 μM) of WP and MP peptides for 2 hours and harvested at different time points. The cells were then washed 4 times with PBS, and whole cell lysates obtained using a Lysis Buffer=50 mM Hepes, 0.1% NP-40, 50 mM NaCl, or the pellet was fractionated by resuspending the pellet in a buffer of 10 mM Hepes-KOH pH=7.9, 10 mM KCl, 0.5 mM DTT, 0.5 mM PMSF, 10 μM Leucpeptin on ice for 10 minutes. After treatment in a microcentrifuge at maximum speed (15 min.), the supernatant was saved as the cytoplasm fraction. The pellet was then resuspended in a buffer of 10 mM Hepes-KOH pH=7.9, 25% glycerol, 410 mM NaCl, 1.5 mM $MgCl_2$, 0.2 mM EDTA, 055 mM DTT, 0.5 mM PMSF on ice. After 20 minutes the sample was again centrifuged at maximum speed for 15 minutes. The supernatant was saved as the nuclear extract. The peptides were visualized by loading the fractions as well the whole cell lysates in 15% tricine SDS-PAGE followed by Western Blot using HA polyclonal antibodies (Sigma).

Coimmunoprecipitations. For in vitro coimmunoprecipitations, Ly1 and 293 T cell nuclear extracts were obtained as described above and incubated with the PB, or WP and MP peptides at a final concentration of 0.12 mg/ml. For in vivo coimmunoprecipitations, 293 T cells were transfected with 4 μg of BCL6 expression vector (REF) using Superfect (Qiagen). Forty-eight hours later the cells were exposed to PB, or the WP or MP peptides for 1 hour, washed 4 times with PBS, and lysed in a buffer of 50 mM Hepes, 0.1% NP-40, 50 mM NaCl. In vitro and in vivo samples were precleared with a mix of Protein G/A agarose beads (Roche, Mannheim, Germany), incubated overnight with BCL6 D-8 monoclonal antibodies (Santa Cruz) and pulled down with G/A agarose beads (Roche) for 2 hours. The pellet was washed 3 times with lysis buffer, resuspended in 2× loading buffer and analyzed by Western blot with HA polyclonal antibodies (Sigma).

Immunofluorescence. $1 \times 10^6$ 293T Cells were plated in 22 mm sterile glass coverslips and placed in 6 well dishes. 24 hours later cells were transfected with 100 ng pEF-BCL6 and/or 200 ng CMX-SMRT or pEF vector using the Superfect reagent (Qiagen). pBluescript was added to 3000 ng per well. Immunostaining was performed as previously reported (REF). BCL6, SMRT and peptides were detected using BCL6 monoclonal antibodies (Dako, Fort Collins, Colo.), SMRT polyclonal antibodies (Upstate Biotechnologies, Waltham, Mass.) or HA polyclonal antibodies (Sigma), followed by donkey anti-mouse and/or anti-rabbit secondary antibodies (Jackson Immuno Research, West Grove, Pa.) conjugated to Cy2 and Cy3 respectively. Confocal microscopy was performed using a Leica AOBS Laser Scanning Confocal Microscope (Leica) in the Albert Einstein Analytical Imaging Facility. Images were captured in each channel independently in non-overlapping spectra. Each experiment was repeated at least 3 times in duplicates and multiple fields imaged and captured.

Reporter assays. 293T cells were plated in a 12 well dish at a density of $2 \times 10^5$ per well or in a 24-well dish at $1 \times 10^5$ per well (Invitrogen, Carlsbad, Calif.), and transfected with 100 ng of either $(GAL4)_5$-TK-Luc or $(BCL6)_4$-TK-Luc and cotransfected with the corresponding expression vectors indicated in the figure legends, plus a renilla reporter construct as an internal control, using Superfect (Qiagen, Valencia, Calif.). After 24 hrs cells were treated with PB, MP or WP at a final concentration 1 μM for 20 hrs, adding fresh peptide every 2.5 hrs. Cells were harvested and dual luciferase assays were performed (Promega, Madison, Wis.) according to the manufacturer's instructions. Luciferase activity was read in a POLARstar Optima microplate luminometer (BMG Labtechnologies, Durham N.C.). All transfections were performed in quadruplicate and repeated at least 3 times. Lysates were subjected to western blot to verify protein expression from transfected vectors.

Real-time PCR. $10^7$ Ly1, Ly8 or Ly4 cells were harvested after no treatment or treatment with PB or 1 μM of WP or MP for 7.5 hours, adding fresh peptide every 2.5 hours. RNA was extracted from the cells using TRIzol® Reagent (Invitrogen). cDNA was synthesized from 10 μg of RNA using the Superscript II™ First Strand cDNA Synthesis System kit (Invitrogen). 1 μl of cDNA for each condition in a final volume of 20 μl was used in real-time PCR analysis using the QuantiTect SYBR® Green PCR kit (QIAGEN) in a DNA Engine Opticon 2® System thermal cycler (MJ Research). mRNA levels of BCL6 target genes were normalized to endogenous levels of HPRT mRNA and calculated relative to buffer using the $\Delta\Delta$Ct method. The peptide treatment of the cells was performed two or three times and real-time PCR experiments were repeated four times with each reaction conducted in triplicate.

The following primers were used:

| | |
|---|---|
| CD80-F: | CATCCTGGGCCATTACCTTA, |
| CD80-R: | TCTCTCTCTGCATCTTGGGG, |
| BCL6-F: | GACTCTGAAGAGCCACCTGC, |
| BCL6-R: | CTGGCTTTTGTGACGGAAAT, |
| CYCLIND2-F: | CCGGACCTAATCCCTCACTC, |
| CYCLIND2-R: | CACACCGATGCAGCTTTCTA, |
| HPRT-F: | AAAGGAACCCCACGAAGTGTT |
| HPRT-R: | TCAAGGGCATATCCTACAACAA |

Chromatin immunoprecipitation. $10 \times 10^7$ Ly1 and Ly8 cells were treated with PB or 1 μM WP or MP peptides for 7.5 hours adding fresh peptide every 2.5 hours. Cells were fixed in 1% formaldehyde (Fisher) (50 mM Hepes pH 8.0, 1mM EDTA, 100 mM NaCl, 0.5 mM EGTA, 37% formaldehyde) for 10 min at room temperature and quenched by 0.125 M glycine for 10 min. Cells were washed twice with ice-cold PBS and resuspended in 4 ml of lysis buffer (1% SDS, 10 mM EDTA pH 8.0, 50 mM Tris-HC1 pH 8.0) at 4° C. for 10 minutes. The lysates were sonicated 5×30 seconds at an amplitude of 55% in a Ultrasonic Dismembrator Model 500 (Fisher) to obtain chromatin fragments with an average size of 300-500 bp, centrifuged at 14,000 rpm for 10 minutes and the supernatants precleared with a mixture of protein A/G agarose beads (Roche). 10% input was collected at this point for later analysis. Specific immunoprecipitations (each on $\sim 10 \times 10^6$ cells) were performed using rabbit polyclonal antibodies for BCL6 (N-3), αN-CoR (H-303) (Santa Cruz), SMRTe, histone 4 pan-acetylated and histone 3 Lysine 9 dimethyl (Upstate Biotechnologies), HA (Sigma), normal rabbit serum (Jackson Immuno Research) or water control overnight at 4° C. DNA-protein complexes were pulled-down by mixing with protein A/G agarose beads at 4° C. for 30 minutes and washed twice with each of the following buffers for 10 minutes at RT: 1.-0.1% SDS, 1% Triton X-100, 2 mM EDTA pH 8.0, 20 mM tris-HCl pH 8.0, 150 mM NaCl; 2.-0.1% SDS, 1% Triton X-100, 2 mM EDTA pH 8.0, 20 mM Tris-HC1 pH 8.0, 500 mM NaCl; 3.-0.25M LiCl, 1% NP-40, 1% Na-Deoxycholate, 1 mM EDTA pH 8,0 and 10 mM tris-HC1 pH 8.0; and finally TE (10 mM Tris, 1 mM EDTA pH 8,0). After the last wash, the beads were resuspended in 100 μl of Elution Buffer (1% SDS, 0.1M $NaHCO_3$), incubated overnight at 65° C. overnight to reverse cross-links and purified using QIAquick PCR purification columns (Qiagen). The resulting DNA fragments were detected by 45 cycles of PCR in a GeneAmp 9700 thermal cycler (Perkin-Elmer-ABI). The following primers were used: MIP-1α promoter: S-5'-ACGATGCTGGGTCAGGTATC-3' AS-5'-AGTGAC-TAGGGCGCTGTGTT-3' (192 by product) and BCL6 exonl: S-5'-GGGTTCTTAGAAGTGGTGATGC-3' AS-5'-TGG-GACTAATCTTCGGCATT-3', and a BCL6 intron 7 negative control S-5'-CGATGAGGAGTTIVGGGATGT-3' AS-5'-TTTCTGGGGGCTCTGTGGACT-3'. These experiments were performed four times and the immunoprecipitations with each antibodies were performed in duplicates in each of the four experiments.

Cell viability. Ly1, Raji and U937 cells were treated with BP, MP, or WP during 48 hours, during that period of time fresh peptide or BP was added every 3 hours, changing the media every 6 hours. Cell viability was determined using the Tox2 XTT bases kit (Sigma) following manufactured instruction. Briefly, XTT solution was added in a final concentration of 20% v/v of the cultured media cells plated in 96 wells plate. The cells were incubated for 4 hours and the $A_{450}$ determined using a MRC Revelation microplate reader (Dinex Technologies, West Sussex, UK). The experiment was performed twice in quadruplicate.

FACS analysis. The cells lines were treated with BP, MP, or WP for 48 hours, with fresh peptide or BP added every 3 hours, and the media changed every 6 hours. After treatment, the cells were harvested, washed with PBS 3% BSA (Sigma), resuspended at $1 \times 10^6$ cells/50 μL in PBS/3% BSA/0.1% $NaN_2$. The cells were immunostained with 5 μl CD10-R-PE and CD38-APC antibodies (Caltag, Burlingame, Calif.) per $10^6$ cells and incubated on ice for 30 min. The cells were then washed twice with PBS/3% BSA/0.1% $NaN_2$ and resuspended in 500 μL PBS/3% BSA/0.1% $NaN_2$. The samples were analyzed on a FACSCalibur or FACScan flow cytometer (Becton Dickinson) using the CellQuest program (BD Bioscience, San Jose, Calif.).

For cell cycle analysis and apoptosis quantification the cells were fixed in cold 70% ethanol and stored until staining. Before staining, the cells were washed twice in PBS and resuspended in 1 ml of PBS. The cells were then stained with 50 μL of propidium iodide (Sigma)(1mg/ml) and 20 μl of ribonuclease A(Sigma)(10 μg/ml). The cells were incubated for 2 hours at 4° C. and then measured by flow cytometry in a FACScan. Cells in pre G1/G0 (hypodiploid DNA) were considered apoptotic. The CellQuest program was used for quantification; cell cycle was analyzed using ModFit software (Verity Software House, Inc, Topsham, Me.). All experiments were performed between 3 and 6 times.

EXAMPLE 3

The Interaction of BCL6 with BCoR

BCoR is a BCL6 co-repressor that was initially identified from a partial clone that interacted with the BCL6 BTB domain in a yeast two-hybrid experiment (Huynh et al., 2000). Genes Dev 14, 1810-1823)). BCoR binds to the BTB domain of BCL6, but does not interact directly with eight other BTB domain proteins that were tested (Huynh et al., 2000). BCoR can potentiate BCL6 repression, possibly through interactions with histone deacetylases (HDACs). Although BCoR has no obvious sequence similarity to the SMRT corepressor, the interactions of SMRT and BCoR to the BCL6 BTB domain are mutually exclusive (Huynh et al., 2000), suggesting that the two corepressors bind to overlapping sites on the BCL6 BTB domain. BCoR may have additional roles with transcriptional partners other than BCL6, and is a key transcriptional regulator during early embryogenesis (Ng et al., 2004).

The initial BCL6 interacting fragment identified in the yeast two-hybrid screen consisted of residues 112-753 of BCoR (Huynh et al., 2000). We expressed subfragments of this region of BCoR as hexahistidine tagged fusion proteins in E. coli, and using the co-purification method described for the identification of the SMRT BBD (Example 1), we found that a purified fusion protein that contained residues 317 to 547 of BCoR bound directly to the BCL6 BTB domain, while fusion proteins containing residues 112 to 342, or 542 to 753 of BCoR did not. The BCoR fragment 317-547 did not bind to the H116A or N21K mutant forms of the BCL6 BTB domain. Similarly, the SMRT BBD does not bind to these two BCL6 mutants in a similar assay (Example 1).

Figure 11:
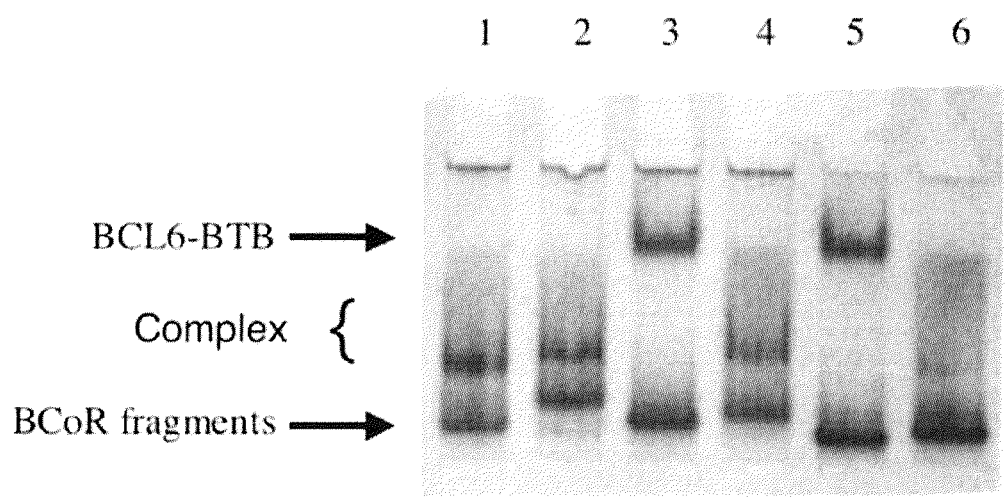
FIG. 11 shows the results of an electrophoretic mobility shift assay for complex formation between the BCL6-3C BTB domain and fusion proteins containing BCoR fragments. Purified BCL6-3C BTB domain was included in all six lanes. Various fragments of BCoR as thioredoxin-6his fusion proteins were included in lanes 1-6 as follows: 1. BCoR 494-518; lane 2 BCoR 498-514; lane 3: BCoR 494-510; lane 4: BCoR 494-514; lane 5: BCoR 506-522; lane 6: BCoR 502-522. BCL6-3C/BCoR complexes were present in lanes 1, 2, 4 and 6.
Figure 12:
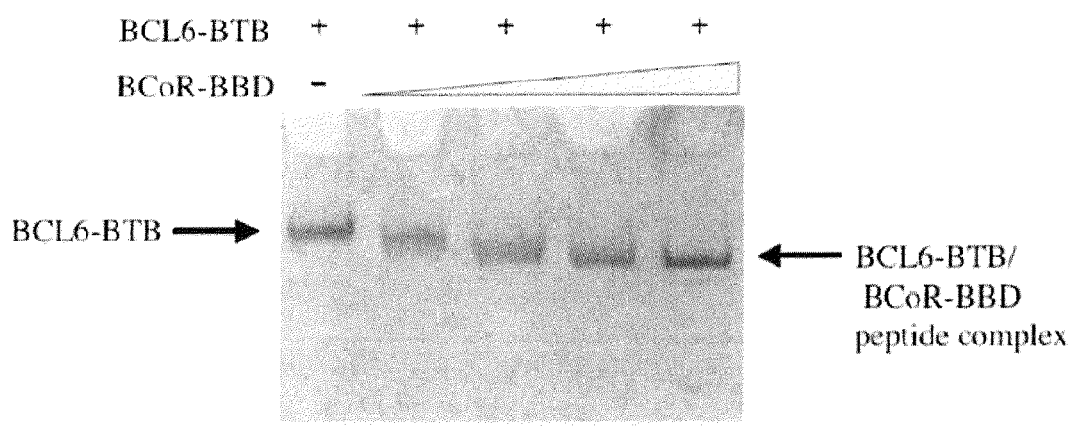
FIG. 12 shows the results of an electrophoretic mobility shift assay showing the effect of increasing amounts of added BCoR-BBD peptide to the BCL6-3C BTB domain.

Further mapping of the minimal BCoR fragment was done with a version of an electrophoretic mobility shift assay (EMSA). Purified BCL6 BTB domain was mixed with a BCoR fragment (either as a fusion protein or as a purified peptide) and incubated at room temperature in a non-denaturing buffer. The mixture was analyzed by non-denaturing polyacrylamide gel electrophoresis (PAGE) and protein bands were visualized with either Coomassie blue staining or silver staining. A change in the position of the BCL6 BTB domain band was indicative of complex formation. FIG. 11 shows a result for a binding experiment with a series of thioredoxin-6his-BCoR fusion proteins. A fragment of BCoR from residues 494-518 (494-CAIYRSEIISTAPSSWV-VPGPSPNE-518) forms a complex with the BCL6 BTB domain, while fragments consisting of residues 494-510 or 506-522 do not interact under these conditions. FIG. 12 shows a titration of increasing amounts of BCoR peptide with a constant amount of BCL6 BTB domain in an EMSA binding assay. Furthermore, peptides of sequence RSEIISTA-PASAVAPGP or RSEIISTAPWSSVVPGP did not result in a shift of the BCL6 BTB band in an EMSA assay. These two sequences correspond to a S507A / W509A / V511A BCoR triple mutation, and to a S507W / W509S BCoR double mutation, respectively. This result demonstrates the importance of the region from 507-SSWVV-511 of BCoR for the interaction with the BCL6 BTB domain.

Figure 13:
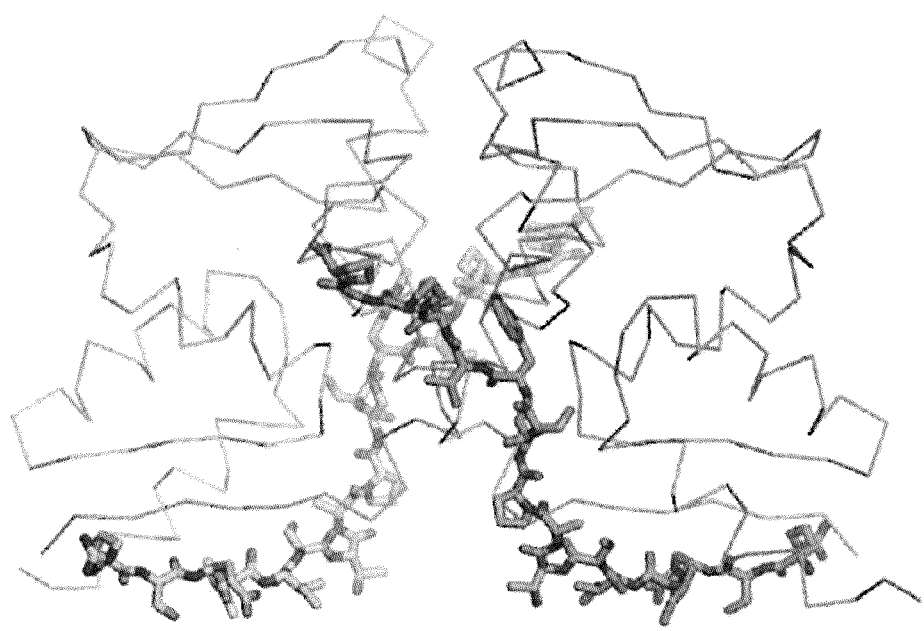
FIG. 13 shows the crystal structure of the BCL6-3C BTB domain in complex with the BCoR 498-514. The BTB domain is in Calpha representation (thin sticks), and the two BCoR peptides are represented with the thicker sticks.

Purified BCL6 BTB domain was cocrystallized with a purified peptide of sequence RSEIISTAPSSWVVPGP, which corresponds to residues 498-514 of BCoR. Crystals were obtained with the hanging drop method by mixing 1 microliter of protein-peptide mixture with 1 microliter of a precipitant solution consisting of sodium acetate, potassium phosphate and sodium phosphate, and equilibrating with the precipitant solution. X-ray diffraction data were collected on crystals at 100 K on a Bruker Proteum CCD detector . Crystallographic statistics are presented in Table 2. The crystals form in space group P6(1)22 with unit cell dimensions of a=b=150.91 Å, c=310.34 Å. The structure was solved by molecular replacement using the BCL6 BTB domain structure. The asymmetric unit contains four crystallographically unique 2:2 BTB -peptide complexes, for a total of eight BTB chains and eight BCoR peptide chains. The structure was refined with CNS and Refmac to a final R factor of 22.37% and an Rfree of 26.32%. The refined model has an rms deviation of 0.008 Å on bond lengths, and 1.3° on bond angles. A representative complex from the crystal structure is shown diagrammatically in FIG. 13.

Figure 14:
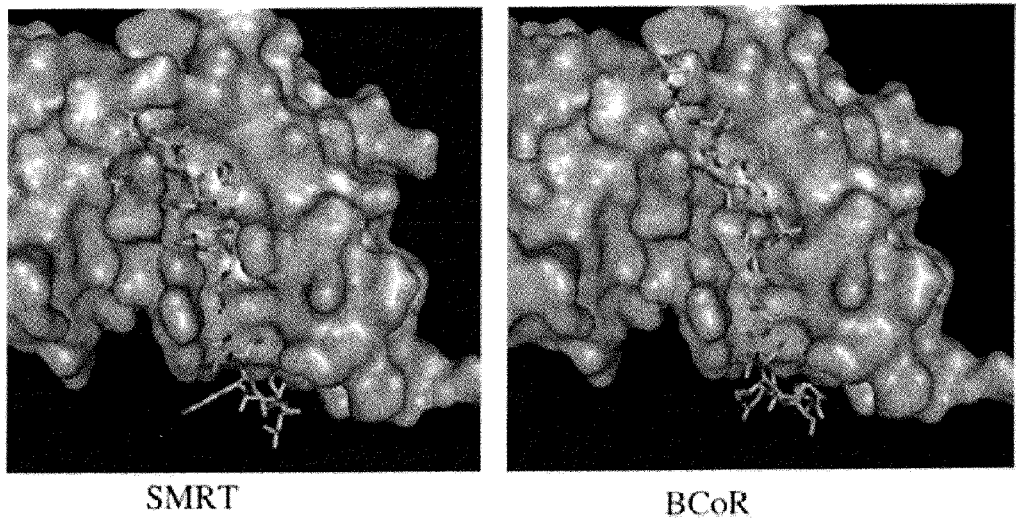
FIG. 14 shows a comparison of the crystal structures of the BCL6-3C BTB domain in complex with the SMRT BBD (left) and the BCoR BBD (right). The BCL6-3C BTB domain dimer is represented as a surface, with His116 highlighted in the center of each panel, just above the stick models. The BBD peptides are shown as stick models.
Figure 15:
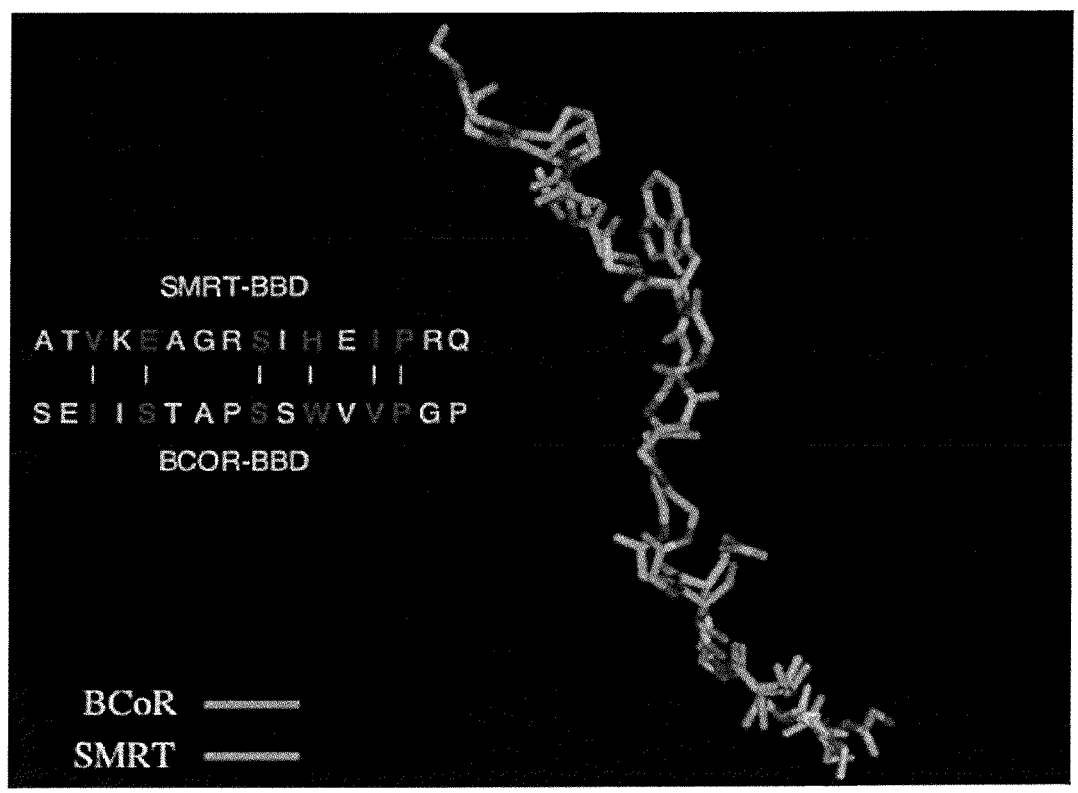
FIG. 15 shows the superposition of the SMRT BBD and BCoR BBD from the crystal structures.

There are small but significant differences in the BCL6 BTB structure in the SMRT and BCoR complexes. The most notable difference is in the position of the side chain of residue His-116, which is positioned above the SMRT peptide in the SMRT/BCL6 complex. In contrast, the BCoR peptide covers His116 in the BCoR/BCL6 complex (FIG. 14). Since binding affinity is to both the SMRT and BCoR BBDs is severely impaired in the BCL6 H116A mutant, the H116/corepressor interactions are important in both cases even though the molecular details are different in each case.

Figure 5:
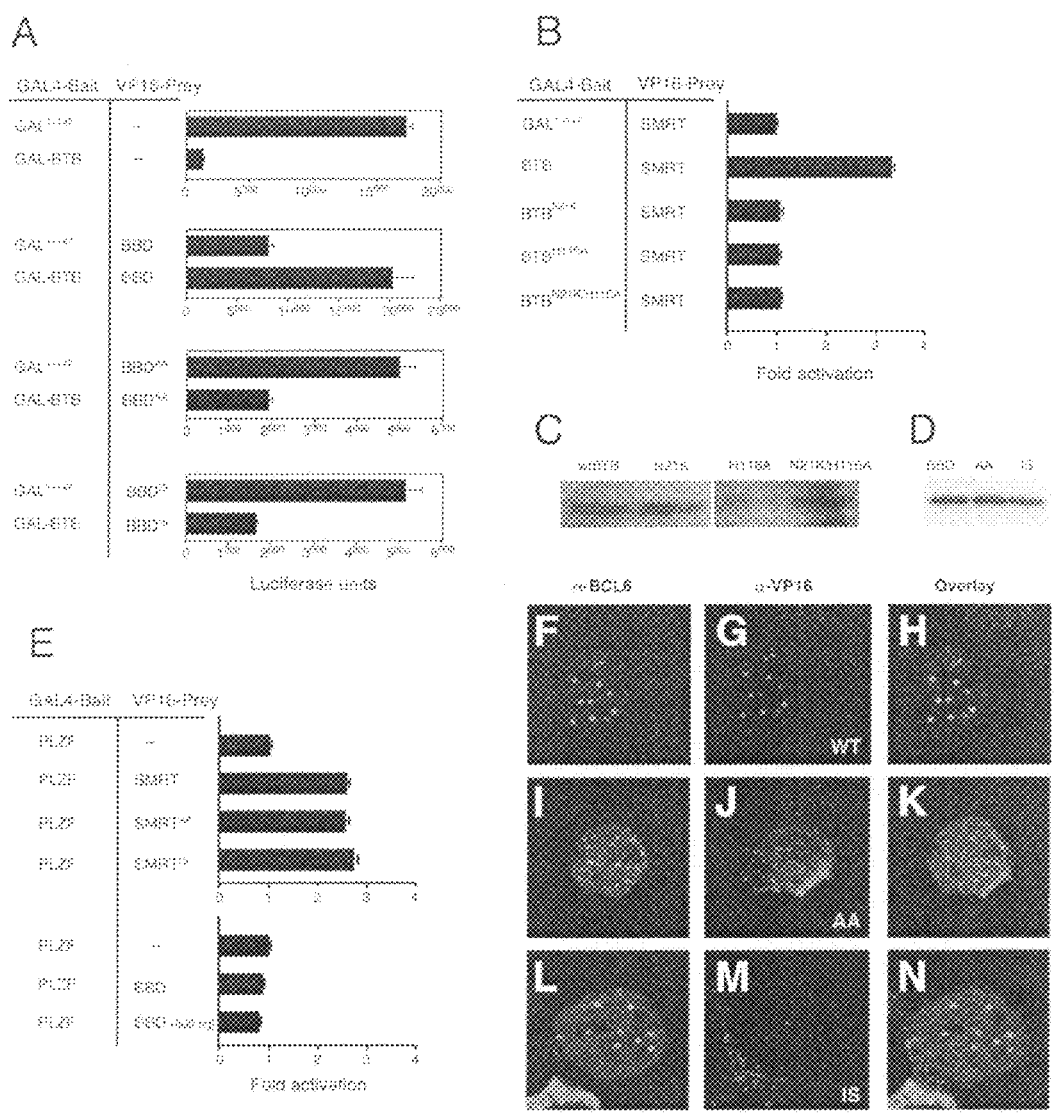
FIG. 5 is graphs, photographs and micrographs showing that the SMRT-BBD interacts with the BCL6 BTB domain in vivo. Mammalian two hybrid assays were performed in 293 T cells by cotransfecting the indicated expression vectors along with 100 ng of a (GAL4)$_5$-TK-Luc reporter and 12.5 ng of a TK-renilla internal control plasmid. Panel A is a graph of experimental results where 25 ng of bait GAL4$^{1\text{-}147}$ or GAL4-BCL6$^{BTB}$ plasmid were transfected either alone or in combination with 300 ng of prey VP16-(SMRT-BBD) fusions. Results are shown as relative luciferase units to show both repression and activation. Panel B is a graph of experimental results where 25 ng of bait plasmid expressing GAL4$^{1\text{-}147}$ alone or fused to wild type or mutant BCL6 BTB domains were cotransfected along with 300 ng of prey plasmid expressing VP16-full-length SMRT fusions. Panel C shows GAL4 immunoblots of 293T cells transfected with 100 ng of wild-type or mutant GAL4-BTB$^{BCL6}$ plasmids. Panel D shows VP16 immunoblots of 293T cells transfected with 300 ng of the wild type or mutant VP16-(SMRT-BBD) plasmids. Panel E is a graph showing experimental results where 50 ng of bait GAL4-PLZF (full-length) plasmid was transfected alone or in combination with 200 ng of prey plasmid expressing VP16-full-length SMRT wild type or point mutants (Top), or 50 ng of bait GAL4-PLZF plasmid was transfected alone or in combination with 200 or 600 ng of prey plasmid expressing VP16-(SMRT-BBD) (Mottom). Panels F-N shows confocal laser scanning microscopy sections collected from 293 T cells cotransfected with a plasmid expressing full length BCL6 along with plasmids expressing wild type (WT) or mutant (AA, IS) VP16-(SMRT-BBD) domain fusions. Immunolocalization was performed using BCL6 monoclonal antibodies with Cyt secondaries (F,I,L), and VP16 polyclonal antibodies with Cy3 secondaries (G,J,M). The overlays of the BCL6 and VP16 (SMRT-BBD) images are shown in panels H,K,N.

Many of the interactions between the SMRT and BCoR BBDs with the BCL6 BTB domain involve main chain residues of the peptides. This explains in part the very low similarity between the SMRT BBD and the BCoR BBD. Nevertheless, amino acid substitutions in both SMRT and BCoR BBDs confirm the importance of key residues in case. The alignment of the two peptides as based on the superposition of the crystal structures is shown in FIG. 5. The most important similarities between the two peptides are at positions His1426 and pro1429 of SMRT, which are equivalent to Trp509 and Pro 512 of BCoR, respectively. Note that although Ser1424 of SMRT is nominally aligned with Ser507 of BCoR, these two residues are in distinct structural environments. This is due in part to the different conformations of BCL6 residue His116 in the two complexes as described above, and in part to significant differences in the path of the peptide backbone in the two corepressor peptides in this region.

TABLE 2

| X-ray diffraction statistics. | |
|---|---|
| Resolution | 3.00 Å |
| Unique reflections | 41133 |
| Redundancy | 3.5 |
| Completeness | 96.3% |
| $<|>/<\sigma|>$ | 13.72 |
| $R_{sym}$ | 6.9% |

Figure 16:
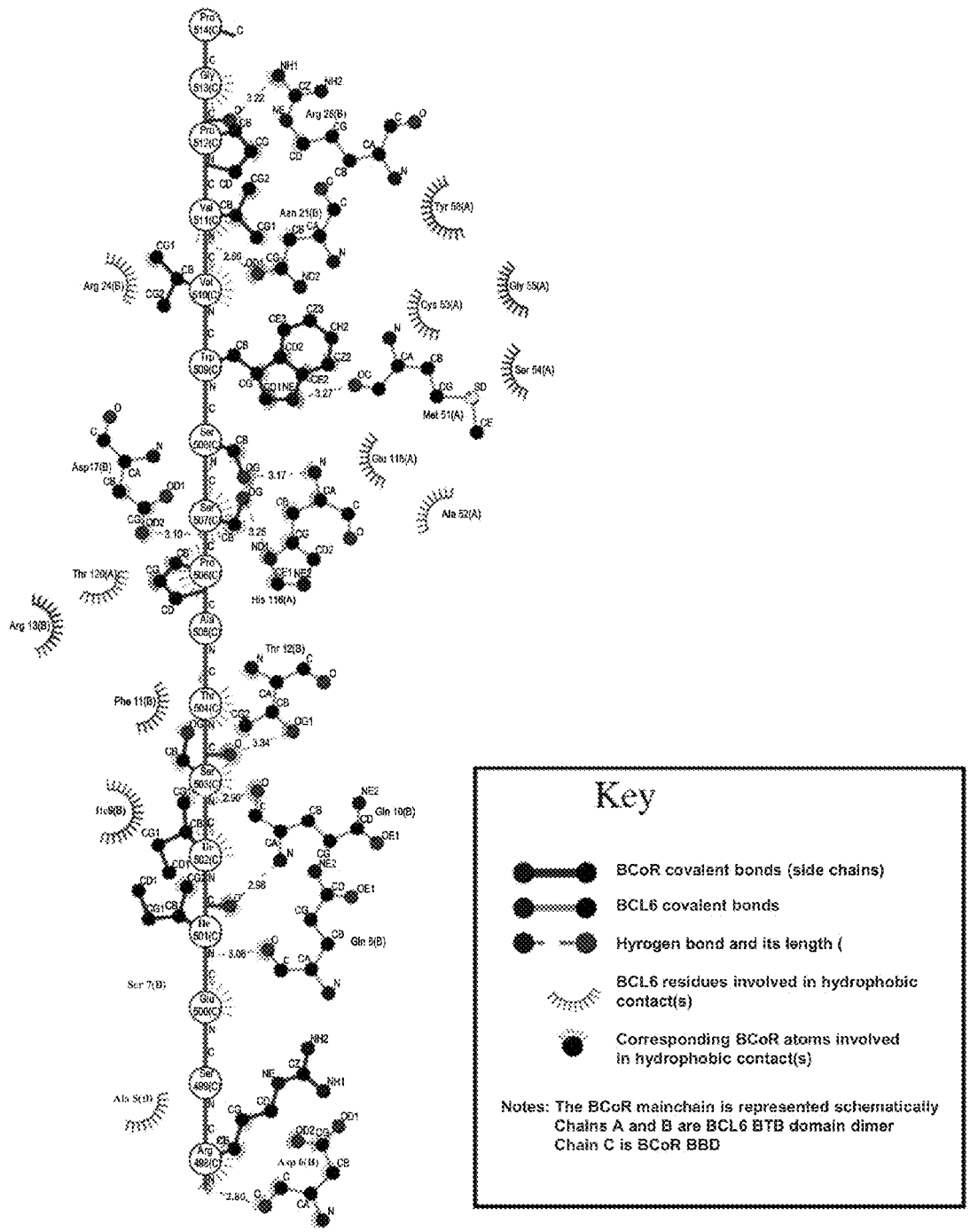
FIG. 16 is a schematic diagram of the interactions of the BCoR peptide with a BCL6-3C BTB dimer (chains A and B).

FIG. 16 shows is a ligplot (Wallace et al., 1995) of the interactions of one of the BCoR peptide with a BCL6 BTB dimer (Chains A and B). There are 8 such equivalent plots, since there are four independent 2:2 complexes in the crystal asymmetric unit. This one is representative of the other eight. The FIG. 16 structure does not include any water molecules (vs. the similar plot at FIG. 4A).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NO:s and other relevant sequence information

SEQ ID NO: 1- SMRT corepressor BCL6 binding peptide- 17mer
lvatvkeagrsiheipr

SEQ ID NO: 2- N-CoR corepressor BCL6 binding peptide- 17mer
gittikemgrsiheipr

SEQ ID NO: 3- BCoR corepressor BCL6 binding peptide- 17mer
yrseiistapsswvvpg

SEQ ID NO: 4- SMRT corepressor BCL6 binding peptide- 21mer
glvatvkeagrsiheipreel SEQ ID NO: 5- N-CoR corepressor BCL6 binding peptide- 21mer
dgittikemgrsiheiprqdi SEQ ID NO: 6- BCoR corepressor BCL6 binding peptide- 21mer
iyrseiistapsswvvpgpsp SEQ ID NO: 7- SMRT corepressor BCL6 binding peptide- 29mer
glvatvkeagrsiheipreelrhtpelpl SEQ ID NO: 8- N-CoR corepressor BCL6 binding peptide- 29mer
dgittikemgrsiheiprqdiltqesrkt SEQ ID NO: 9- BCoR corepressor BCL6 binding peptide- 29mer
iyrseiistapsswvvpgpspneenngk SEQ ID NO: 10- peptide consensus sequence
(l/g/y)(v/i/r)(a/t/s)(t/e)(v/i)(k/i)(e/s)(a/m/t)(g/a)(r/p)s(i/s)(h/w)(e/v)(i/v)p(r/g)

SEQ ID NO: 11- wt BCL6 BTB domain
```
        10          20          30          40          50          60
MASPADSCIQ FTRHASDVLL NLNRLRSRDI LTDVVIVVSR EQFRAHKTVL MACSGLFYSI 70          80          90         100         110         120
FTDQLKCNLS VINLDPEINP EGFCILLDFM YTSRLNLREG NIMAVMATAM YLQMEHVVDT

129
CRKFIKASE
```

SEQ ID NO: 12- mutant BCL6 BTB domain that can be expressed
in a soluble form, e.g., in *E. coli*. The mutations are C8Q,
C67R and C84N). The extra "GS" residues at the N terminus are
non-natural residues introduced by cloning strategy.
GSADSQIQFT RHASDVLLNL NRLRSRDILT DVVIVVSREQ FRAHKTVLMA

CSGLFYSIFT DQLKRNLSVI NLDPEINPEG FNILLDFMYT SRLNLREGNI

MAVMATAMYL QMEHVVDTCR KFIKASE

Alignment of wt and mutated BCL6 BTB domain (wt on top).
Three wt Cys were changed by site-directed mutagenesis:
C8Q, C67R and C84N.
```
MASPADSCIQFTRHASDVLLNLNRLRSRDILTDVVIVVSREQFRAHKTVLMACSGLFYSIFTDQ
  GSADSQIQFTRHASDVLLNLNRLRSRDILTDVVIVVSREQFRAHKTVLMACSGLFYSIFTDQ LKCNLSVINLDPEINPEGFCILLDFMYTSRLNLREGNIMAVMATAMYLQMEHVVDTCRKF
LKRNLSVINLDPEINPEGFNILLDFMYTSRLNLREGNIMAVMATAMYLQMEHVVDTCRKF

IKASE
IKASE
```

---

What is claimed is:

1. A method of determining whether a test compound inhibits corepressor binding to B-cell lymphoma 6 (BCL6), the method comprising determining whether the test compound binds to both BTB domains of a BCL-6 BTB dimer, and identifying the test compound as an inhibitor or not of corepressor binding to BCL6, wherein a compound that binds to both BTB domains of a BCL-6 BTB dimer is an inhibitor of corepressor binding to BCL6 and wherein each BTB domain comprises the amino acid sequence set forth in SEQ ID NO:11 or SEQ ID NO:12.

2. The method of claim 1, wherein the test compound is an organic compound less than 1000 molecular weight.

3. The method of claim 1, wherein the test compound is an organic compound less than 3000 molecular weight.

4. The method of claim 1, wherein the test compound is an aptamer.

5. The method of claim 1, wherein the test compound is a peptide or peptide mimetic.

6. The method of claim 5, wherein the peptide or mimetic comprises SEQ ID NO:10.

7. The method of claim 5, wherein the peptide or mimetic comprises SEQ ID NO:1.

8. The method of claim 5, wherein the peptide or mimetic comprises SEQ ID NO:2.

9. The method of claim 5, wherein the peptide or mimetic comprises SEQ ID NO:3.

10. The method of claim 1, wherein the BCL-6 BTB dimer is part of a BCL-6 homodimer.

11. The method of claim 1, wherein the compound binds to a B1' and to a α1' of a first BTB domain of the BCL6 BTB dimer and to an α2 and to an α3 and to an α6 of a second BTB domain of the BCL6 BTB dimer.

12. The method of claim 1, wherein the test compound binds to an asparagine residue position 21 of SEQ ID NO: 11.

13. The method of claim 1, wherein the test compound binds to a histidine at residue position 116 of SEQ ID NO: 11.

14. The method of claim 1, wherein determining whether the test compound binds to both BTB domains of a BCL-6 BTB dimer is effected using X-ray crystallography.

* * * * *

SEQUENCE LISTING

<160> NUMBER OF SEQ ID NOS: 34

<210> SEQ ID NO 1
<211> LENGTH: 17
<212> TYPE: PRT
<213> ORGANISM: Homo sapiens

<400> SEQUENCE: 1

```
Leu Val Ala Thr Val Lys Glu Ala Gly Arg Ser Ile His Glu Ile Pro
1               5                   10                  15
Arg

<210> SEQ ID NO 2
<211> LENGTH: 17
<212> TYPE: PRT
<213> ORGANISM: Homo sapiens

<400> SEQUENCE: 2

Gly Ile Thr Thr Ile Lys Glu Met Gly Arg Ser Ile His Glu Ile Pro
1               5                   10                  15
Arg

<210> SEQ ID NO 3
<211> LENGTH: 17
<212> TYPE: PRT
<213> ORGANISM: Homo sapiens

<400> SEQUENCE: 3

Tyr Arg Ser Glu Ile Ile Ser Thr Ala Pro Ser Ser Trp Val Val Pro
1               5                   10                  15
Gly

<210> SEQ ID NO 4
<211> LENGTH: 21
<212> TYPE: PRT
<213> ORGANISM: Homo sapiens

<400> SEQUENCE: 4

Gly Leu Val Ala Thr Val Lys Glu Ala Gly Arg Ser Ile His Glu Ile
1               5                   10                  15
Pro Arg Glu Glu Leu
            20

<210> SEQ ID NO 5
<211> LENGTH: 21
<212> TYPE: PRT
<213> ORGANISM: Homo sapiens

<400> SEQUENCE: 5

Asp Gly Ile Thr Thr Ile Lys Glu Met Gly Arg Ser Ile His Glu Ile
1               5                   10                  15
Pro Arg Gln Asp Ile
            20

<210> SEQ ID NO 6
<211> LENGTH: 21
<212> TYPE: PRT
<213> ORGANISM: Homo sapiens

<400> SEQUENCE: 6

Ile Tyr Arg Ser Glu Ile Ile Ser Thr Ala Pro Ser Ser Trp Val Val
1               5                   10                  15
Pro Gly Pro Ser Pro
            20

<210> SEQ ID NO 7
<211> LENGTH: 29
<212> TYPE: PRT
<213> ORGANISM: Homo sapiens
```

```
-continued

<400> SEQUENCE: 7

Gly Leu Val Ala Thr Val Lys Glu Ala Gly Arg Ser Ile His Glu Ile
1               5                   10                  15

Pro Arg Glu Glu Leu Arg His Thr Pro Glu Leu Pro Leu
            20                  25

<210> SEQ ID NO 8
<211> LENGTH: 29
<212> TYPE: PRT
<213> ORGANISM: Homo sapiens

<400> SEQUENCE: 8

Asp Gly Ile Thr Thr Ile Lys Glu Met Gly Arg Ser Ile His Glu Ile
1               5                   10                  15

Pro Arg Gln Asp Ile Leu Thr Gln Glu Ser Arg Lys Thr
            20                  25

<210> SEQ ID NO 9
<211> LENGTH: 28
<212> TYPE: PRT
<213> ORGANISM: Homo sapiens

<400> SEQUENCE: 9

Ile Tyr Arg Ser Glu Ile Ile Ser Thr Ala Pro Ser Ser Trp Val Val
1               5                   10                  15

Pro Gly Pro Ser Pro Asn Glu Glu Asn Asn Gly Lys
            20                  25

<210> SEQ ID NO 10
<211> LENGTH: 17
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Leu, Gly, or Tyr
<220> FEATURE:
<221> NAME/KEY: MISC_FEATURE
<222> LOCATION: (2)..(2)
<223> OTHER INFORMATION: Xaa is Val, Ile, or Arg
<220> FEATURE:
<221> NAME/KEY: MISC_FEATURE
<222> LOCATION: (3)..(3)
<223> OTHER INFORMATION: Xaa is Ala, Thr, or Ser
<220> FEATURE:
<221> NAME/KEY: MISC_FEATURE
<222> LOCATION: (4)..(4)
<223> OTHER INFORMATION: Xaa is Thr or Glu
<220> FEATURE:
<221> NAME/KEY: MISC_FEATURE
<222> LOCATION: (5)..(5)
<223> OTHER INFORMATION: Xaa is Val or Ile
<220> FEATURE:
<221> NAME/KEY: MISC_FEATURE
<222> LOCATION: (6)..(6)
<223> OTHER INFORMATION: Xaa is Lys or Ile
<220> FEATURE:
<221> NAME/KEY: MISC_FEATURE
<222> LOCATION: (7)..(7)
<223> OTHER INFORMATION: Xaa is Glu or Ser
<220> FEATURE:
<221> NAME/KEY: MISC_FEATURE
<222> LOCATION: (8)..(8)
<223> OTHER INFORMATION: Xaa is Ala, Met, or Thr
<220> FEATURE:
<221> NAME/KEY: MISC_FEATURE
<222> LOCATION: (9)..(9)
<223> OTHER INFORMATION: Xaa is Gly or Ala
<220> FEATURE:
```

```
<221> NAME/KEY: MISC_FEATURE
<222> LOCATION: (10)..(10)
<223> OTHER INFORMATION: Xaa is Arg or Pro
<220> FEATURE:
<221> NAME/KEY: MISC_FEATURE
<222> LOCATION: (12)..(12)
<223> OTHER INFORMATION: Xaa is Ile or Ser
<220> FEATURE:
<221> NAME/KEY: MISC_FEATURE
<222> LOCATION: (13)..(13)
<223> OTHER INFORMATION: Xaa is His or Trp
<220> FEATURE:
<221> NAME/KEY: MISC_FEATURE
<222> LOCATION: (14)..(14)
<223> OTHER INFORMATION: Xaa is Glu or Val
<220> FEATURE:
<221> NAME/KEY: MISC_FEATURE
<222> LOCATION: (15)..(15)
<223> OTHER INFORMATION: Xaa is Ile or Val
<220> FEATURE:
<221> NAME/KEY: MISC_FEATURE
<222> LOCATION: (17)..(17)
<223> OTHER INFORMATION: Xaa is Arg or Gly

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 11
<211> LENGTH: 129
<212> TYPE: PRT
<213> ORGANISM: Homo sapiens

<400> SEQUENCE: 11

Met Ala Ser Pro Ala Asp Ser Cys Ile Gln Phe Thr Arg His Ala Ser
1               5                   10                  15

Asp Val Leu Leu Asn Leu Asn Arg Leu Arg Ser Arg Asp Ile Leu Thr
                20                  25                  30

Asp Val Val Ile Val Val Ser Arg Glu Gln Phe Arg Ala His Lys Thr
            35                  40                  45

Val Leu Met Ala Cys Ser Gly Leu Phe Tyr Ser Ile Phe Thr Asp Gln
50                  55                  60

Leu Lys Cys Asn Leu Ser Val Ile Asn Leu Asp Pro Glu Ile Asn Pro
65                  70                  75                  80

Glu Gly Phe Cys Ile Leu Leu Asp Phe Met Tyr Thr Ser Arg Leu Asn
                85                  90                  95

Leu Arg Glu Gly Asn Ile Met Ala Val Met Ala Thr Ala Met Tyr Leu
            100                 105                 110

Gln Met Glu His Val Val Asp Thr Cys Arg Lys Phe Ile Lys Ala Ser
        115                 120                 125

Glu

<210> SEQ ID NO 12
<211> LENGTH: 127
<212> TYPE: PRT
<213> ORGANISM: Artificial
<220> FEATURE:
<223> OTHER INFORMATION: synthetic mutant

<400> SEQUENCE: 12

Gly Ser Ala Asp Ser Gln Ile Gln Phe Thr Arg His Ala Ser Asp Val
1               5                   10                  15

Leu Leu Asn Leu Asn Arg Leu Arg Ser Arg Asp Ile Leu Thr Asp Val
                20                  25                  30
```

-continued

Val Ile Val Val Ser Arg Glu Gln Phe Arg Ala His Lys Thr Val Leu
            35                  40                  45

Met Ala Cys Ser Gly Leu Phe Tyr Ser Ile Phe Thr Asp Gln Leu Lys
 50                  55                  60

Arg Asn Leu Ser Val Ile Asn Leu Asp Pro Glu Ile Asn Pro Glu Gly
 65                  70                  75                  80

Phe Asn Ile Leu Leu Asp Phe Met Tyr Thr Ser Arg Leu Asn Leu Arg
                 85                  90                  95

Glu Gly Asn Ile Met Ala Val Met Ala Thr Ala Met Tyr Leu Gln Met
                100                 105                 110

Glu His Val Val Asp Thr Cys Arg Lys Phe Ile Lys Ala Ser Glu
            115                 120                 125

<210> SEQ ID NO 13
<211> LENGTH: 93
<212> TYPE: DNA
<213> ORGANISM: Artificial
<220> FEATURE:
<223> OTHER INFORMATION: oligonucleotide for plasmid construction

<400> SEQUENCE: 13
catggctggt ggccacggtg aaggaggcgg gccgctccat ccatgagatc ccgcgcgagg    60
agctgcggca cacgcccgag ctgccccctgg ccc                                93

<210> SEQ ID NO 14
<211> LENGTH: 93
<212> TYPE: DNA
<213> ORGANISM: Artificial
<220> FEATURE:
<223> OTHER INFORMATION: oligonucleotide for plasmid construction

<400> SEQUENCE: 14
tcgagggcca gggcagctc gggcgtgtgc cgcagctcct cgcgcgggat ctcatggatg    60
gagcggcccg cctccttcac cgtggccacc agc                                 93

<210> SEQ ID NO 15
<211> LENGTH: 93
<212> TYPE: DNA
<213> ORGANISM: Artificial
<220> FEATURE:
<223> OTHER INFORMATION: oligonucleotide for plasmid construction

<400> SEQUENCE: 15
catggctggt ggccacggtg aaggaggcgg gccgctccat ccatgcagct gcagctgagg    60
agctgcggca cacgcccgag ctgccccctgg ccc                                93

<210> SEQ ID NO 16
<211> LENGTH: 93
<212> TYPE: DNA
<213> ORGANISM: Artificial
<220> FEATURE:
<223> OTHER INFORMATION: oligonucleotide for plasmid construction

<400> SEQUENCE: 16
tcgagggcca gggcagctc gggcgtgtgc cgcagctcct cagctgcagc tgcatggatg    60
gagcggcccg cctccttcac cgtggccacc agc                                 93

<210> SEQ ID NO 17
<211> LENGTH: 20
<212> TYPE: DNA
<213> ORGANISM: Artificial

```
<220> FEATURE:
<223> OTHER INFORMATION: primer

<400> SEQUENCE: 17
catcctgggc cattacctta                                               20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tctctctctg catcttgggg                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
gactctgaag agccacctgc                                               20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ctggcttttg tgacggaaat                                               20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ccggacctaa tccctcactc                                               20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
cacaccgatg cagctttcta                                               20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
aaaggaaccc cacgaagtgt t                                             21
```

-continued

```
<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
tcaagggcat atcctacaac aa                                              22

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
acgatgctgg gtcaggtatc                                                 20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
agtgactagg gcgctgtgtt                                                 20

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
gggttcttag aagtggtgat gc                                              22

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tgggactaat cttcggcatt                                                 20

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
cgatgaggag tttcgggatg t                                               21

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
```

```
tttctggggg ctctgtggac t                                              21

<210> SEQ ID NO 31
<211> LENGTH: 25
<212> TYPE: PRT
<213> ORGANISM: Homo sapiens

<400> SEQUENCE: 31

Cys Ala Ile Tyr Arg Ser Glu Ile Ile Ser Thr Ala Pro Ser Ser Trp
1               5                   10                  15

Val Val Pro Gly Pro Ser Pro Asn Glu
            20                  25

<210> SEQ ID NO 32
<211> LENGTH: 17
<212> TYPE: PRT
<213> ORGANISM: Homo sapiens

<400> SEQUENCE: 32

Arg Ser Glu Ile Ile Ser Thr Ala Pro Ala Ser Ala Val Ala Pro Gly
1               5                   10                  15

Pro

<210> SEQ ID NO 33
<211> LENGTH: 17
<212> TYPE: PRT
<213> ORGANISM: Homo sapiens

<400> SEQUENCE: 33

Arg Ser Glu Ile Ile Ser Thr Ala Pro Trp Ser Ser Val Val Pro Gly
1               5                   10                  15

Pro

<210> SEQ ID NO 34
<211> LENGTH: 17
<212> TYPE: PRT
<213> ORGANISM: Homo sapiens

<400> SEQUENCE: 34

Arg Ser Glu Ile Ile Ser Thr Ala Pro Ser Ser Trp Val Val Pro Gly
1               5                   10                  15

Pro
```